United States Patent
Pang et al.

(10) Patent No.: US 9,090,602 B2
(45) Date of Patent: Jul. 28, 2015

(54) CLASS OF NEAR INFRARED OPTICAL PROBES FOR BIOLOGICAL APPLICATIONS

(71) Applicant: The University of Akron, Akron, OH (US)

(72) Inventors: Yi Pang, Copley, OH (US); Yongqian Xu, Akron, OH (US)

(73) Assignee: The University of Akron, Akron, OH (US)

(*) Notice: Subject to any disclaimer, the term of this patent is extended or adjusted under 35 U.S.C. 154(b) by 0 days.

(21) Appl. No.: 13/622,109

(22) Filed: Sep. 18, 2012

(65) Prior Publication Data

US 2014/0080168 A1    Mar. 20, 2014

(51) Int. Cl.
| | |
|---|---|
| *C07D 413/14* | (2006.01) |
| *C07D 263/56* | (2006.01) |
| *C07D 413/10* | (2006.01) |
| *C07F 3/06* | (2006.01) |
| *G01N 33/52* | (2006.01) |
| *A61B 5/145* | (2006.01) |
| *A61B 5/1455* | (2006.01) |
| *G01N 33/84* | (2006.01) |

(52) U.S. Cl.
CPC ............... *C07D 413/14* (2013.01); *A61B 5/145* (2013.01); *A61B 5/1455* (2013.01); *A61B 5/14546* (2013.01); *C07D 263/56* (2013.01); *C07D 413/10* (2013.01); *C07F 3/06* (2013.01); *G01N 33/52* (2013.01); *G01N 33/84* (2013.01)

(58) Field of Classification Search
CPC .. A61B 5/145; A61B 5/1455; A61B 5/14546; C07D 263/56; C07D 413/10; C07D 413/14; C07F 3/06; G01N 33/52; G01N 33/84
See application file for complete search history.

(56) References Cited

FOREIGN PATENT DOCUMENTS

WO    WO 2010075003 A1 *  7/2010

OTHER PUBLICATIONS

Yongqian Xu, Qin Liu, Bairui Dou, Brian Wright, Jingyun Wang, Yi Pang, Zn2+ Binding-Enabled Excited State Intramolecular Proton Transfer: A Step toward New Near-Infrared Fluorescent Probes for Imaging Applications, 2012, Advanced Healthcare Materials, vol. 1, Issue 4, pp. 485-492 (Abst. and Supplementary Information) published online May 11, 2012.*

(Continued)

*Primary Examiner* — Blaine Lankford
*Assistant Examiner* — Trent R Clarke
(74) *Attorney, Agent, or Firm* — Renner Kenner Greive Bobak Taylor & Weber

(57) ABSTRACT

2,5-Bis(benzoxazol-2'-yl)benzene-1,4-diol derivatives (Zinhbo derivatives) are used to detect zinc ions and have particular application in vivo and in vitro. Zinhbo derivatives upon excitation give a florescence response emission that can be used to determine the presence of zinc cation in solution. Zinhbo derivatives complexed with zinc cations upon excitation can produce a florescence response emission in the visible and near infrared range. Zinhbo derivatives complexed with zinc cations exhibit a large stoke shift between the excitation and emission wavelengths.

6 Claims, 20 Drawing Sheets
(15 of 20 Drawing Sheet(s) Filed in Color)

(56) References Cited

OTHER PUBLICATIONS

Yongqian Xu and Yi Pang, Zn2+-triggered excited-state intramolecular proton transfer: a sensitive probe with near-infrared emission from bis(benzoxazole) derivative, 2011, Dalton Trans., vol. 40, pp. 1503-1509.*

Elena Luzina, Jerzy Sepioł, Yuriy N. Svartsov, and Anna Grabowska, Effect of alkyl substituents on excited state intramolecular proton transfer dynamics of jet-cooled bis(benzoxazolyl)phenoles, 2007, The Journal of Chemical Physics, vol. 126, pp. 194308-1-7.*

* cited by examiner

CLASS OF NEAR INFRARED OPTICAL PROBES FOR BIOLOGICAL APPLICATIONS

FIELD OF THE INVENTION

The present invention generally relates to compounds for the detection of zinc ions, the synthesis of compounds for the detection of zinc ions, compositions for the detection zinc ions, and methods for detecting zinc ions.

BACKGROUND OF THE INVENTION

Organic fluorescent probes are useful labeling for biomolecules. For in vivo applications, molecular imaging reagent is required to be biocompatible and to emit optical signals in the near infrared (NIR) region (700-900 nm), as NIR light can penetrate more deeply into biological tissues. On the practical side, optical imaging is dependent on the availability of the luminescent NIR reagents that exhibit high quantum yield, chemical and optical stability, and suitable pharmacological properties including aqueous solubility, specific binding, and low toxicity. At present time, most of the NIR probes are based on cyanine dyes, whose emission maxima are in the region of 650-900 nm. A notable drawback for the parent cyanine dyes is their small Stokes shift (typically about 20-50 nm), which hampers their broad application.

Among the new emerging design principles applied in fluorescent sensing, excited-stated intramolecular proton transfer (ESIPT) has recently received considerable attention due to its unique photophysical properties. Different from other organic chromophores, ESIPT molecules exhibit dual emissions from both the excited enol and keto tautomers, which are well separated from each other. In addition, emission of ESIPT dyes generally have large Stokes shift (ca. 150-200 nm), making them the ideal candidates for fluorescent sensors. Some ESIPT-based molecules, including 2-(2'-hydroxyphenyl)benzoxazole (HBO) and 2-(2'-hydroxyphenyl)benzimidazole (HBI), have been reported for cations and anion sensing. Most studies utilize ESIPT turn-off mechanisms since the interaction with a cation (or anion) removes the phenolic proton, thereby inhibiting ESIPT and resulting in blue-shifted fluorescence. Removal of the phenolic proton during metal chelation, however, permanently turns-off ESIPT. Thus far, only a few examples are known to utilize ESIPT turn-on mechanism in the chemosensor design, which involves the deprotection of the protected hydroxyl group. Among the known examples, nearly all ESIPT-based probes give emission in the visible region (400-650 nm).

As the second most abundant transition-metal ion in the human body, the $Zn^{2+}$ ion is a component of enzymes and proteins, and plays an important role in various biological processes. In order to discover the vital roles of $Zn^{2+}$ in biological processes, there is growing demand for sensing $Zn^{2+}$ in living systems. Although many fluorescent chemosensors for $Zn^{2+}$ cation have been studied, few near-infrared (NIR) fluorescent zinc probes are available to give emission in the desired 700-900 nm range. An ideal $Zn^{2+}$ probe requires not only NIR emission (to minimize autofluorescence) but also large Stokes shift (for improved signal detection). It is thus desirable to incorporate the ESIPT process into the sensing scheme. Achieving the ESIPT emission signals in the NIR region, however, remains an attractive and challenging task.

SUMMARY OF THE INVENTION

One embodiment of this invention provides a composition for detection of zinc ions defined by the formula:

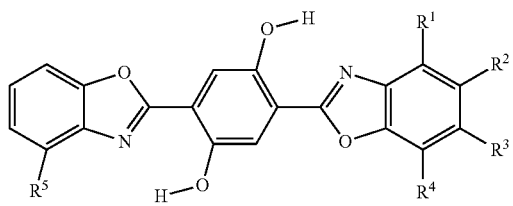

where $R^1$ is a hydrogen atom or an electron withdrawing group; $R^2$, $R^3$, and $R^4$ are each individually selected from the group consisting of a hydrogen atom, an electron withdrawing group, and an electron donating group; and $R^5$ is a chelator group capable of forming a complex with a zinc cation.

Yet another embodiment provides a method for detecting the presence of zinc ions in solution, the method comprising the steps of contacting a solution with a Zinhbo derivative defined by the formula:

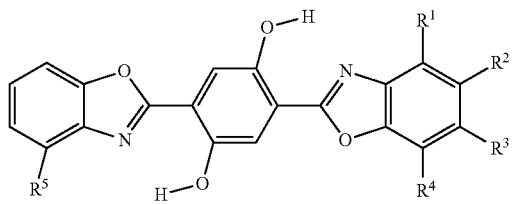

where $R^1$ is a hydrogen atom or an electron withdrawing group; $R^2$, $R^3$, and $R^4$ are each individually selected from the group consisting of a hydrogen atom, an electron withdrawing group, and an electron donating group; and $R^5$ is a chelator group capable of forming a complex with a zinc cation, exciting the solution with an excitation wavelength, and measuring a florescence response emission in the visible or near infrared range.

Yet another embodiment provides a method for detecting the presence of zinc ions, the method comprising the steps of contacting living cells or a living organism with a Zinhbo derivative, exciting the solution with an excitation wavelength, and measuring a florescence response emission in the visible or near infrared range.

This invention also provides a method as in paragraph [0008] wherein the Zinhbo derivative defined by the formula:

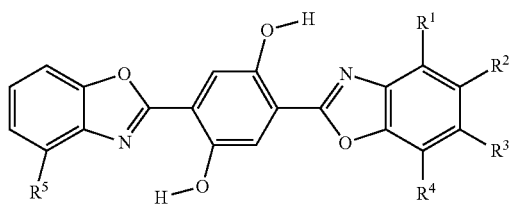

where $R^1$, $R^2$, $R^3$, and $R^4$ are each individually selected from the group consisting of a hydrogen atom, an electron withdrawing group, and an electron donating group; and $R^5$ is a chelator group capable of forming a complex with a zinc cation.

This invention also provides a method as in paragraph [0009] wherein the Zinhbo derivative includes an $R^2$, $R^3$, and $R^4$ that are hydrogen atoms and an $R^1$ that is and electron donating group.

This invention also provides a method as in paragraph [0010] wherein the electron donating group is an alkyl group.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

In one or more embodiments, the invention relates to 2,5-bis(benzoxazol-2'-yl)benzene-1,4-diol derivatives for the detection of zinc ions. In other embodiments, the invention relates to compositions for the detections of zinc ions. In still other embodiments, the invention relates to methods for the detection of zinc ions using 2,5-bis(benzoxazol-2'-yl)benzene-1,4-diol derivatives. These compositions and methods will have particular application in vivo and in vitro.

The applicants have found that 2,5-bis(benzoxazol-2'-yl)benzene-1,4-diol derivatives can give turn-on excited state intramolecular proton transfer (ESIPT) fluorescence upon addition of zinc cations. A unique feature of 2,5-bis(benzoxazol-2'-yl)benzene-1,4-diol derivatives is that the sensor molecule contains two 2-(2'-hydroxyphenyl)benzoxazole units. In its zinc complex only one 2-(2'-hydroxyphenyl)benzoxazole unit binds to a zinc cation, while the other 2-(2'-hydroxyphenyl)benzoxazole unit is retained for ESIPT. Zinc binding not only turns on the fluorescence but also enables the ESIPT emission with a large Stokes shift. In one or more embodiments, the 2,5-bis(benzoxazol-2'-yl)benzene-1,4-diol derivative binds a zinc cation that is a $Zn^{2+}$ cation. For further discussion on florescence of 2,5-bis(benzoxazol-2'-yl)benzene-1,4-diol derivatives see Y. Xu, Y. Pang, Chem. Commun., 46 4070-4072 (Apr. 15, 2010) and Y. Xu, Y. Pang, Dalton Transactions, 40 1503-1509 (Feb. 1, 2011) which are incorporated in their entirety by reference.

Figure 4:
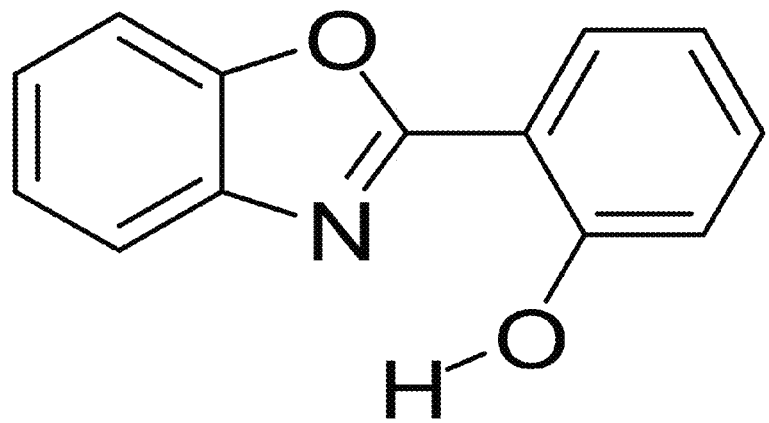
FIG. 4 provides the molecular structure of an HBO unit.

In one or more embodiments, that 2,5-bis(benzoxazol-2'-yl)benzene-1,4-diol derivatives are compounds which include a dihydroxyphenyl group bound to two benzoxazole groups. In one or more embodiments, a benzoxazole group of the 2,5-bis(benzoxazol-2'-yl)benzene-1,4-diol derivative may include one or more groups that form a complex with a zinc ion. In one or more embodiments, a benzoxazole group of the 2,5-bis(benzoxazol-2'-yl)benzene-1,4-diol derivative may include one or more substituents that are electron donating groups. In these or other embodiments, a benzoxazole group of the 2,5-bis(benzoxazol-2'-yl)benzene-1,4-diol derivative may include one or more substituents that are electron withdrawing groups. A 2,5-bis(benzoxazol-2'-yl)benzene-1,4-diol derivative may also be considered a compound which includes two 2-(2'-hydroxyphenyl) benzoxazole units that share a dihydroxyphenyl group. A 2-(2'-hydroxyphenyl) benzoxazole unit may also be referred to as a HBO unit (FIG. 4). 2,5-Bis(benzoxazol-2'-yl)benzene-1,4-diol derivatives may be referred to as Zinhbo derivatives.

In one or more embodiments, the Zinhbo derivative may be defined by the following formula 1:

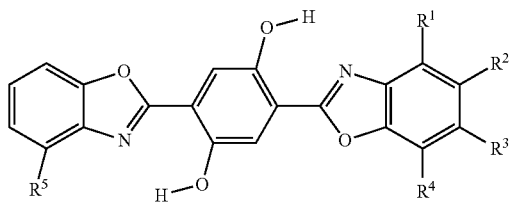

where $R^1$, $R^2$, $R^3$, and $R^4$ are each individually selected from the group consisting of a hydrogen atom, an electron withdrawing group, and an electron donating group; and $R^5$ is a chelator group capable of forming a complex with a zinc cation.

Figure 3:
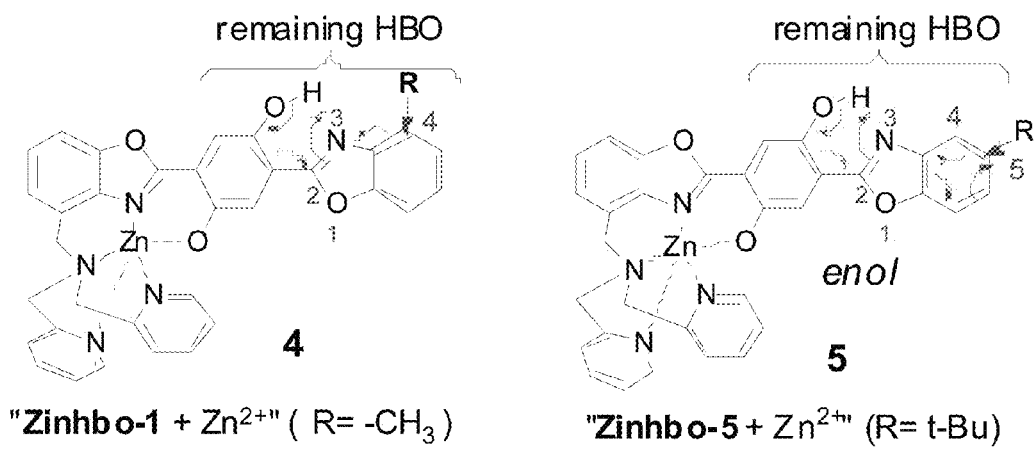
FIG. 3 provides the electron flow for the excited state intramolecular proton transfer (ESIPT) for two embodiments of Zinhbo molecules.

In one or more embodiments, the $R^1$ of formula 1 is not an electron donating group. In these and other embodiments, $R^1$ of formula 1 is not an alkyl group. In these or other embodiments, $R^1$ of formula 1 is an electron withdrawing group or a hydrogen atom. Though not to be bound by any particular theory, it is believed that, when $R^1$ of formula 1 is an electron donating group the electron flow required for the excited-state intramolecular proton transfer is partially perturbed by the electron donating effect (FIG. 3).

Electron donating groups, also referred to as activating groups, are groups that add electron density to the benzene ring. Electron donating groups are typically classified by their strength into groups consisting of strong electron donating groups, moderate electron donating groups, and weak electron donating groups.

Examples of strong electron donating groups include, but are not limited to, an alcohol group (—OH), an oxyl group (—O—), an amino group (—NH$_2$), alkylamino groups (—NHR), and dialkylamino groups (—NR$_2$). Examples of moderate electron donating groups include, but are not limited to, alkoxy groups (—OR) and amide groups (—NHCOR). Examples of weak electron donating groups include, but are not limited to, alkyl groups (—R). For the purpose of defining donating groups R can be defined as an alkyl group. In one or more embodiments alkyl groups include linear or branched hydrocarbons with a carbon chain length of 1 to 6 carbons. Specific examples of alkyl groups include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Specific examples of alkylamino groups suitable for use as an electron donating group include, but are not limited to, methylamino, ethylamino, propylamino, isopropylamino, isobutylamino, tert-butylamino, n-butylamino, sec-butylamino, isopentylamino, tertpentylamino, n-pentylamino, sec-pentylamino, terthexylamino, n-hexylamino, isohexylamino, and sec-hexylamino.

Specific examples of dialkylamino groups suitable for use as an electron donating group include, but are not limited to, dimethylamino, diethylamino, dipropylamino, diisopropylamino, diisobutylamino, di-tert-butylamino, di-n-butylamino, di-sec-butylamino, diisopentylamino, tertpentylamino, di-n-pentylamino, di-sec-pentylamino, di-tert-hexylamino, n-hexylamino, diisohexylamino, di-sec-hexylamino, methylethylamino, methylpropylamino, methylisopropylamino, methylisobutylamino, tert-butylmethylamino, n-butylmethylamino, ethylpropylamino, ethylisopropylamino, ethylisobutylamino, tert-butylethylamino, and n-butylethylamino.

In one or more embodiments, alkyl groups suitable for use as an electron donating group include linear or branched hydrocarbons with a carbon chain length of 1 to 6 carbons. Specific examples of alkyl groups suitable for use as an electron donating group include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Specific examples of alkoxy groups suitable for use as an electron donating group include, but are not limited to, methoxy, ethoxy, propoxy, isopropoxy, isobutoxy, tert-butoxy, n-butoxy, sec-butoxy, isopentoxy, tertpentoxy, n-pentoxy, sec-pentoxy, terthexoxy, n-hexoxy, isohexoxy, and sec-hexoxy.

Specific examples of amide groups suitable for use as an electron donating group include, but are not limited to, acetamide, propanamide, butyramide, isobutyramide, pentanamide, isopentanamide, and tertpentanamide.

Electron withdrawing groups, also referred to as deactivating groups, are groups that remove electron density from the benzene ring. Electron withdrawing groups are typically classified by their strength into groups consisting of strong electron withdrawing groups, moderate electron withdrawing groups, and weak electron withdrawing groups.

Examples of strong electron withdrawing groups include, but are not limited to, a nitro group (—NO$_2$), quaternary amine groups (—NR$_3$), and trihalomethane groups (—CX$_3$). Examples of moderate electron withdrawing groups include, but are not limited to, a cyano group (—C≡N), a sulfonate group (—SO$_3$H), a carboxylic acid group (—COOH), ester groups (—COOR), an aldehyde group (—CHO), and ketone groups (—COR). Examples of weak electron withdrawing groups include, but are not limited to, halide atoms (—X). For the purpose of defining electron withdrawing groups R can be defined as an alkyl group described above.

Specific examples of ester groups suitable for use as an electron withdrawing group include, but are not limited to, methanoate, ethanoate, propanoate, butanoate, pentanoate, and hexanoate.

Specific examples of ketone groups suitable for use as an electron withdrawing group include, but are not limited to, ethanoyl, propanoyl, butanoyl, pentanoyl, and hexanoyl.

Specific examples of halide atoms suitable for use as an electron withdrawing group include, but are not limited to, a fluoride atom, a chloride atom, a bromide atom, an iodide atom, and an astatide atom.

In one ore more embodiments, the chelator group capable of forming a complex with a zinc cation include linear or cyclic polyamine chelating groups. Specific examples of groups that form complexes with zinc ions include, but are not limited to, linear polyamine chelators such as di-2-picolylamine, and cyclic polyamine chelators such as 1,4,7,10-tetrazacyclododecane.

In one or more embodiments, 3 of $R^1$, $R^2$, $R^3$, and $R^4$ of formula 1 are hydrogen atoms. In particular embodiments, where $R^1$, $R^3$, and $R^4$ of formula 1 are hydrogen atoms, the Zinhbo derivative may be defined by the following formula 2:

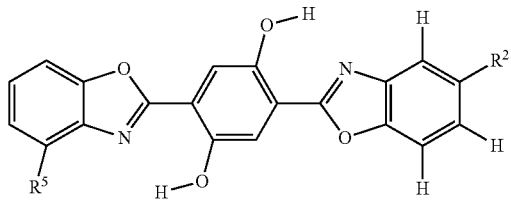

where $R^2$ is an electron withdrawing group or an electron donating group, and $R^5$ is a chelator group capable of forming a complex with a zinc cation.

In particular embodiments, where the $R^5$ group of formula 2 is a di-2-picolylamine group, the Zinhbo derivative may be defined by the following formula 3:

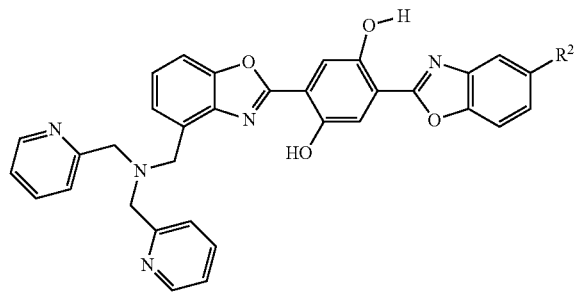

where $R^2$ is an electron withdrawing group or an electron donating group.

Zinhbo derivatives, when excited with an excitation wavelength, will emit one or more fluorescence responses. In one or more embodiments, the uncomplexed Zinhbo derivative, compared to the complexed Zinhbo derivative, has a weak florescence response in the visible region. In one or more embodiments, the Zinhbo derivative complexed with a zinc cation, compared to the uncomplexed Zinhbo derivative, has an increased florescence response in the visible region. In one or more embodiments, the Zinhbo derivative complexed with a zinc cation has florescence response in the near infrared region not detectable in the uncomplexed Zinhbo derivative. In these or other embodiments, the Zinhbo derivative in the presence of zinc cations, compared to the uncomplexed Zinhbo derivative, will produce an increased emission in the visible region, near infrared region, or both the visible and near infrared region.

Zinhbo derivatives when excited with an excitation wavelength will emit one or more fluorescence responses. In one or more embodiments, the uncomplexed Zinhbo derivative will have two florescence response maxima in the visible region. In one or more embodiments, the Zinhbo derivative complexed with a zinc cation has a single florescence response maxima in the visible region. In one or more embodiments, the Zinhbo derivative complexed with a zinc cation has a florescence response maxima in the near infrared region. In these or other embodiments, the Zinhbo derivative in the presence of zinc cations will produce an emission in the visible region, near infrared region, or both the visible and near infrared region.

Figure 2:
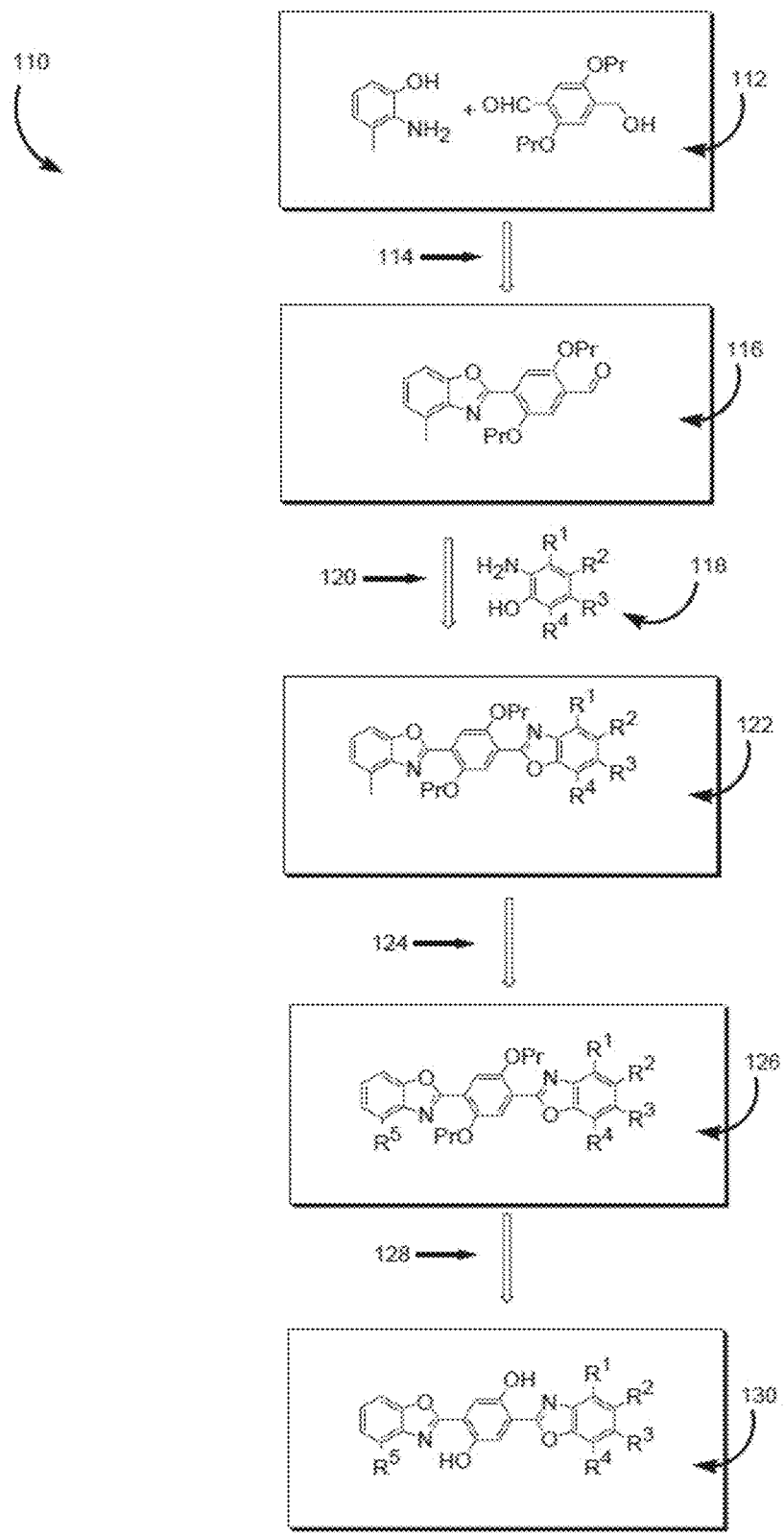
FIG. 2 provides a general reaction scheme for the preparation of a Zinhbo derivative according to one or more embodiments of this invention.

A Zinhbo derivative may be prepared through the process 110 of FIG. 2 where the reactants 112 are reacted in a alcohol solvent under reflux at step 114. The alcohol solvent is then evaporated and the product is reacted with 2,3-dichloro-5,6-dicyano-1,4-benzoquinone (DDQ) in methylene chloride, then purifide, and treated with pyridium chlorochromate in methylene chloride to yield intermediate product 116. The intermediate product 116 is purified and then reacted with reactant 118 in toluene under reflux to make intermediate product 122. Intermediate product 122 is then purified and reacted at step 124 with N-bromosuccinimide to brominate the pendant methyl group. The brominated pendant methyl group is then reacted with (a) an amine compound that includes a group capable of chelating and (b) $Na_2CO_3$ in dry THF to create the $R^5$ chelator group capable of forming a complex with a zinc cation of intermediate compound 126. The protecting groups are then removed to produce at step 128 to produce the Zinbo derivative 130.

In process 110 of FIG. 2, $R^1$, $R^2$, $R^3$, and $R^4$ are each individually selected from the group consisting of a hydrogen atom, an electron withdrawing group, and an electron donating group; $R^5$ is a chelator group capable of forming a complex with a zinc cation; and Pr is a protecting group. A protecting group is a group used to protect a sensitive group from reacting (in this instance an alcohol group) during a reaction step in a synthesis of a molecule. The protecting group is later removed. Examples of protecting groups include, but are not limited to, alkyl groups and silyl groups.

In one or more embodiments, the Zinhbo derivatives may be used to detect the presence of zinc cations in a test sample. The test sample is a substance that may contain zinc ions. The Zinhbo derivative is contacted with the test sample. An excitation wavelength is then applied to the test sample. In the presence of zinc cations a Zinhbo derivative will form a complex with a zinc ion and the Zinhbo derivative will give an emission wavelength or florescence response that corresponds to complexed Zinhbo derivative, thus indicating the presence of zinc cations in the test sample. In the absence of zinc cations, the Zinhbo derivative will not form a complex and the Zinhbo derivative will give an emission wavelength corresponding to uncomplexed Zinhbo derivatives.

The test sample may be obtained directly from a source to be tested for the presence of zinc cations, or it may be created by dissolving or diluting a source to be tested for the presence of zinc cations.

In one or more embodiments, solvents suitable for the creation of test samples include solvents selected from the group consisting of aqueous solvents, protic solvents, and organic solvents. Examples of aqueous solvents include, but are not limited to, water and pH buffered solutions. Examples of protic solvents include, but are not limited to, lower alcohols, such as methanol and ethanol. Examples of organic solvents include, but are not limited to, tetrahydrofuran and methylene chloride.

Figure 1:
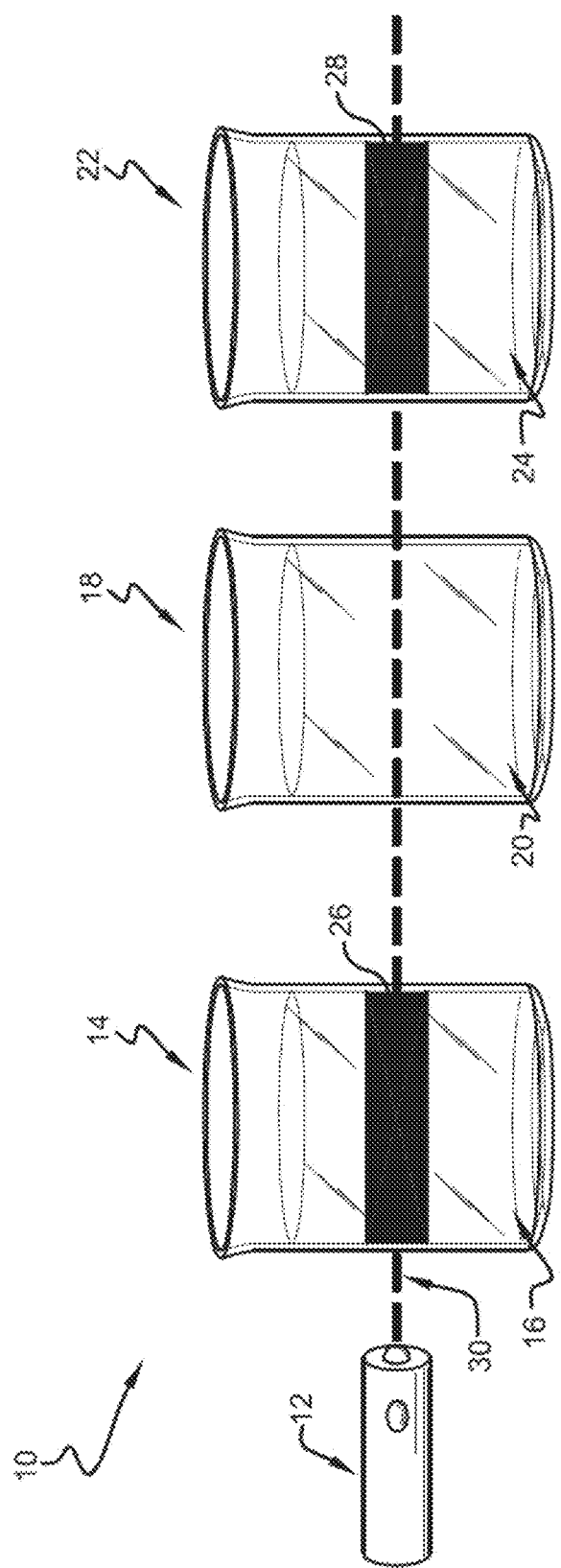
FIG. 1 provides a general schematic of a method for testing one or more test solutions for the presence of zinc cation in accordance with this invention.

As a unique feature, the Zinhbo derivative give two emission signals upon binding to zinc cations; one emission in the visible region, and the other emission signal in the near infrared region. One advantage of this method is that it can be used to test a large number of test samples all at the same time. This is shown in FIG. 1, showing a method 10, wherein a light source 12 directs light 30 (a stimulated emission of photons) through a first container 14 holding a test sample 16, a second container 18 holding a test sample 20 and a third container 22 holding a test sample 24. As seen, the first container 14 and third container 28 hold test samples 16 that include zinc, because the light 30 causes fluorescence whose color can be seen visually as at 26 (container 14) and 28 (container 22). The second container 18 does not show fluorescence and thus, the test sample 20 placed therein does not include zinc. Although the response of the colored fluorescence signal can be detected visually by the naked eye, the signals in the near infrared region can give more sensitive detection.

In one or more embodiments, the Zinhbo derivative may be used to detect the presence of zinc cations in vivo. The presence of zinc cations in vivo by testing an entire living organism or a portion of an organism that contains living cells for the presence of zinc cations.

The Zinhbo derivative may be added in vivo, by contacting living cells with a Zinhbo derivative. In one or more embodiments, the living cells that are contacted by the Zinhbo derivative are tissues or part of a living organism. Examples of methods of contacting living cells with a Zinhbo derivative include, but are not limited to, incubating cultured cells with the Zinhbo derivative in a culture medium, injecting Zinhbo derivative into living cells. Examples of methods of contacting a living organism with a Zinhbo derivative include, but are not limited to, treating a portion of water containing an aquatic animal with a Zinhbo derivative. Other methods of contacting a living organism with a Zinhbo derivative include, but are not limited, having the living organism ingest the Zinhbo derivative and injecting the Zinhbo derivative into the living organism.

In one or more embodiment, the presence of zinc cations in vivo may be found by exciting the living cells or living organism with an excitation wavelength. If zinc ions are present in vivo the Zinhbo derivative will form a complex with a zinc ion and the Zinhbo derivative will give an emission wavelength, or florescence response, corresponding to complexed Zinhbo derivatives and the presence of zinc cations will be detected. In the absence of zinc cations, the Zinhbo derivative will not form a complex and the Zinhbo derivative will give an emission wavelength corresponding to uncomplexed Zinhbo derivatives.

In one or more embodiments, the Zinhbo derivative may be used to detect the presence of free zinc cations in vivo. Free zinc cations refer to the unbound zinc cations in a cell. Zinc in a cell may be bound to proteins. Zinc imbalance in certain tissues is found to be associated with several chronic diseases such as diabetes and Alzheimer's disease. Examples of tissues where free zinc cations may be found includes, but is not limited to, brain, insulin, intestine, and retina.

In particular embodiments, when the Zinhbo derivative is used to detect the presence of zinc cations or free zinc cations in vivo, it is beneficial to detect the response emission in the near infrared wavelengths. Detection in the near infrared wavelengths is advantageous because wavelengths in the near infrared region can penetrate deeper into biological tissues. In some embodiments, wavelengths in the infrared region can penetrate up to about 4 cm of biological tissue. In some embodiments, wavelengths in the infrared region can penetrate up to about 3 cm of biological tissue. In one or more embodiments, the Zinhbo derivative may be used to detect zinc cations in an organism by scanning an organism with a near infrared light.

The ability of wavelengths in the infrared region to penetrate biological tissue allows for Zinhbo derivatives to be used to scan an organism for zinc or free zinc cations. In one or more embodiments, an entire organism can be scanned for the presence of zinc cations by delivering a Zinhbo derivative internally to an organism, exciting the entire organism with an excitation wavelength, and detecting the florescence response emission. In one or more embodiments, a portion organism can be scanned for the presence of zinc cations by delivering a Zinhbo derivative internally to an organism, exciting a portion of the organism with an excitation wavelength, and detecting the florescence response emission. By scanning an organism or a portion of an organism for zinc cations it allows a map of zinc content within the organism to be determined which may benefit in the treating and research of diseases associated with the imbalance of zinc with in the organism's tissues, such as cancer, diabetes and Alzheimer's disease.

The amount of Zinhbo derivative used to detect zinc ions can also be defined in terms of nM. In one or more embodiments, the amount of Zinhbo derivative in solution is 0.01 nM to 100 nM. In other embodiments, the amount of Zinhbo derivative in solution is 0.1 nM to 50 nM. In still other embodiments, the amount of Zinhbo derivative in solution is 0.2 nM to 5 nM.

In one or more embodiments, the Zinhbo derivatives are excited with an excitation wavelength from about 400 nm to about 550 nm. In one or more embodiments, the Zinhbo derivatives are excited with an excitation wavelength from about 430 nm to about 500 nm. In particular embodiment, the Zinhbo derivatives are excited with an excitation wavelength at about 480 nm.

In one or more embodiments, the Zinhbo derivative complexed with a zinc cation has a florescence response emission in the near infrared region. In one or more embodiments, the Zinhbo derivative has a florescence response emission in the range of about 700 to about 900 nm. In one or more embodiments, the Zinhbo derivative has a florescence response emission in the range of about 710 to about 800 nm. In these or other embodiments the Zinhbo derivative has a florescence response emission at about 760 nm.

In one or more embodiments, the Zinhbo derivative complexed with a zinc cation has an increased florescence response emission in the visible region. In one or more embodiments, the Zinhbo derivative has a florescence response emission in the range of about 500 nm to about 700 nm. In one or more embodiments, the Zinhbo derivative has a florescence response emission in the range of about 530 nm to about 590 nm. In these or other embodiments the Zinhbo derivative has a florescence response emission at about 550 nm.

In one or more embodiments, the Zinhbo derivative will exhibit a fluorescence response emission when excited in the visible region. In these and other embodiments, the Zinhbo derivative complexed with a zinc cation have two or more florescence response emissions in the range of about 500 nm to about 900 nm. In these embodiments, the presence of zinc cations can be detected by emissions in the visible region, near infrared region, or both the visible and near infrared region.

In one or more embodiments, the uncomplexed Zinhbo derivative has a florescence response emission when excited in the range of about 510 to about 570 nm. In one or more embodiments, the uncomplexed Zinhbo derivative has two florescence response emission maxima in the range of about 510 to about 570 nm. In these or other embodiments the Zinhbo derivative has a florescence response emission at about 520 nm and a florescence response emission at about 560 nm.

EXAMPLES

In order to facilitate the in vivo study of zinc-related biology, it is essential to develop a zinc-selective sensor that exhibits both near-infrared (NIR) emission and larger Stokes shift. A fluorescent sensor, Zinhbo-5, has been constructed by using bis(benzoxazole) ligand with 2,2'-dipicolylamine (DPA) as metal ion receptor. In aqueous solution, Zinhbo-5 exhibits high sensitivity (Kd=2.58 nM$^2$) and selectivity for Zn$^{2+}$ cation, revealing about 14-fold fluorescence enhancement upon zinc binding to give green emission. Remarkably, Zn$^{2+}$ binding to Zinhbo-5 switches on the excited state intramolecular proton transfer (ESIPT), producing the desirable near-infrared region (over 710 nm) with large Stokes shift (ca. 240 nm). The new probe is demonstrated to be useful for in vivo imaging of the intracellular Zn$^{2+}$ ion. The Zinhbo-5 is also useful for detecting zinc ion distribution during the development of living zebrafish embryos.

Figure 5:
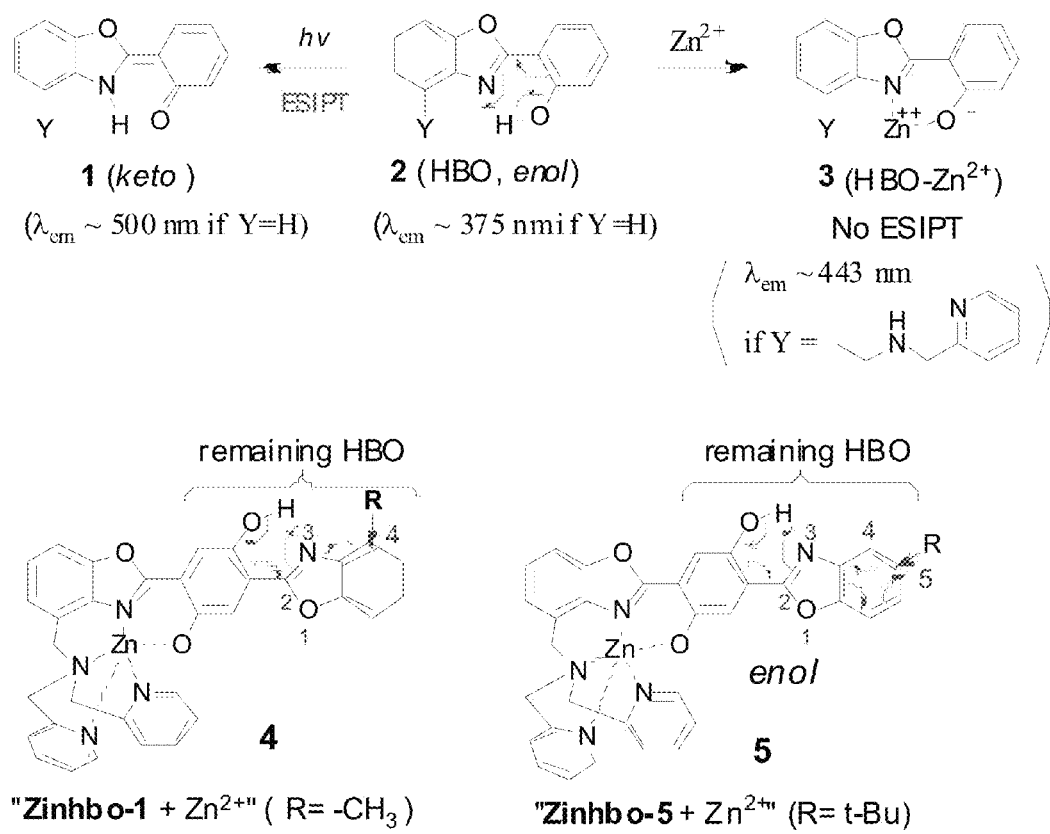
FIG. 5 provides the electron flow for the excited state intramolecular proton transfer (ESIPT) for various HBO and Zinhbo molecules.

With reference to FIG. 5, our recent study illustrates that 2,5-bis(benzoxazol-2'-yl)benzene-1,4-diol derivative (Zinhbo-1) can give turn-on ESIPT fluorescence upon addition of zinc(II) cation. A unique feature in Zinhbo-1 is that the sensor molecule contains two HBO units. In its zinc complex 4, only one HBO unit is used to bind Zn$^{2+}$ cation, while the other HBO is retained for ESIPT. Zinc binding not only turns on the fluorescence but also enables the ESIPT emission with a large Stokes shift (ca 230 nm). The NIR emission band from Zinhbo-1-Zn$^{2+}$ complex (at ~710 nm), however, is very weak, preventing its practical applications. In the Zn$^{2+}$ complex 4 (FIG. 3), the electron flow for the ESIPT on the remaining HBO unit is indicated by arrows. The alkyl group at "position 4" of the benzoxazole unit appears to exert opposite electronic effect on the benzoxazole "nitrogen" atom (also indicated by appropriate arrows). This adverse effect could be partially reduced by moving the alkyl to "position 5" as shown in the compound 5. In order to test this hypothesis, we designed the synthesis of Zinhbo-5. Upon addition of Zn$^{2+}$ cation, Zinhbo-5 exhibits remarkably strong fluorescent turn-on of the desirable NIR signal along with large Stokes' shift, thereby enabling this dye's practical applications in biological cells.

Results and Discussion

Figure 6:
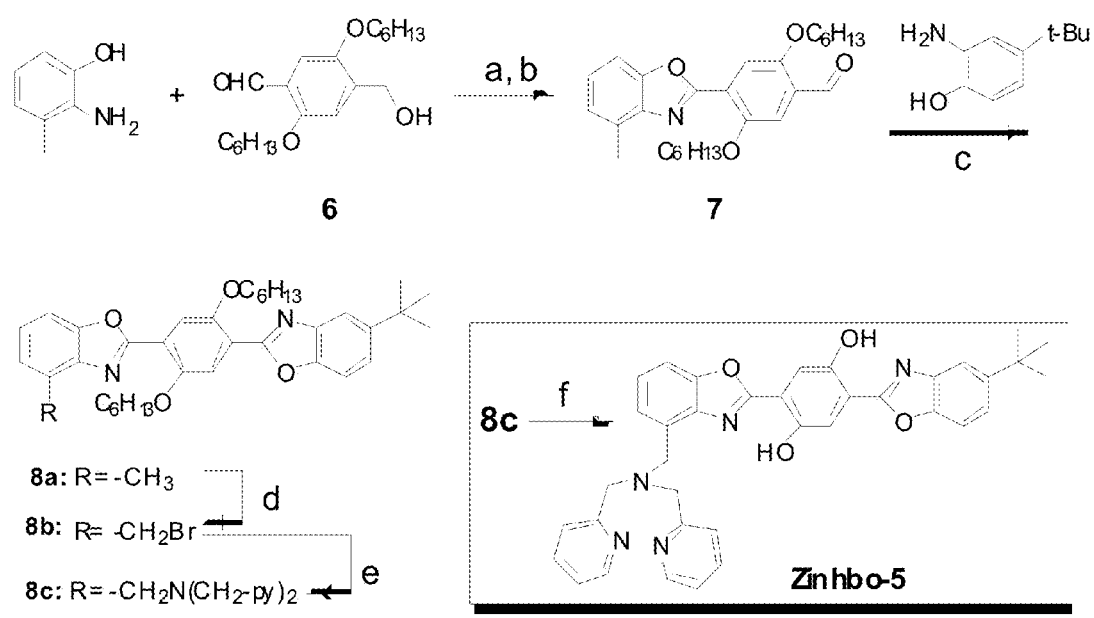
FIG. 6 provides the synthesis scheme of an embodiment of the invention, Zinhbo-5 sensor, under the following reagents and conditions: a) (i) MeOH, 5A Molecular Sieves, Reflux, 81.8%; (ii) DDQ, $CH_2Cl_2$, 86.9%; b) PCC, $CH_2Cl_2$; c) (i) Toluene, Reflux, (ii) iodobenzene diacetate (IBD), $CH_2Cl_2$, 64.6%; d) NBS, AIBN, $CCl_4$; e) DPA, $Na_2CO_3$, THF, 12.1%; f) $BBr_3$, $CH_2Cl_2$, 17.0%.

Sensor Zinhbo-5 was synthesized as shown in FIG. 6, which includes a sequential construction of two HBO units as shown in compound 7 and 8. With reference to FIG. 6, the reagents and reaction conditions were as follows: a) (i) MeOH, 5A Molecular Sieves, Reflux, 81.8%; (ii) DDQ, CH$_2$Cl$_2$, 86.9%; b) PCC, CH$_2$Cl$_2$; c) (i) Toluene, Reflux, (ii) iodobenzene diacetate (IBD), CH$_2$Cl$_2$, 64.6%; d) NBS, AIBN, CCl$_4$; e) DPA, Na$_2$CO$_3$, THF, 12.1%; f) BBr$_3$, CH$_2$Cl$_2$, 17.0%. The sensor includes the di-2-picolylamine (DPA) group near a HBO, since DPA is a classical membrane-permeable chelator with high selectivity for Zn$^{2+}$ over alkali and alkaline-earth metal ions (occurring in higher concentrations) in biological samples.

Zinc Binding of Zinhbo-5
Ligand-to-Metal Ratio.

Figure 7:
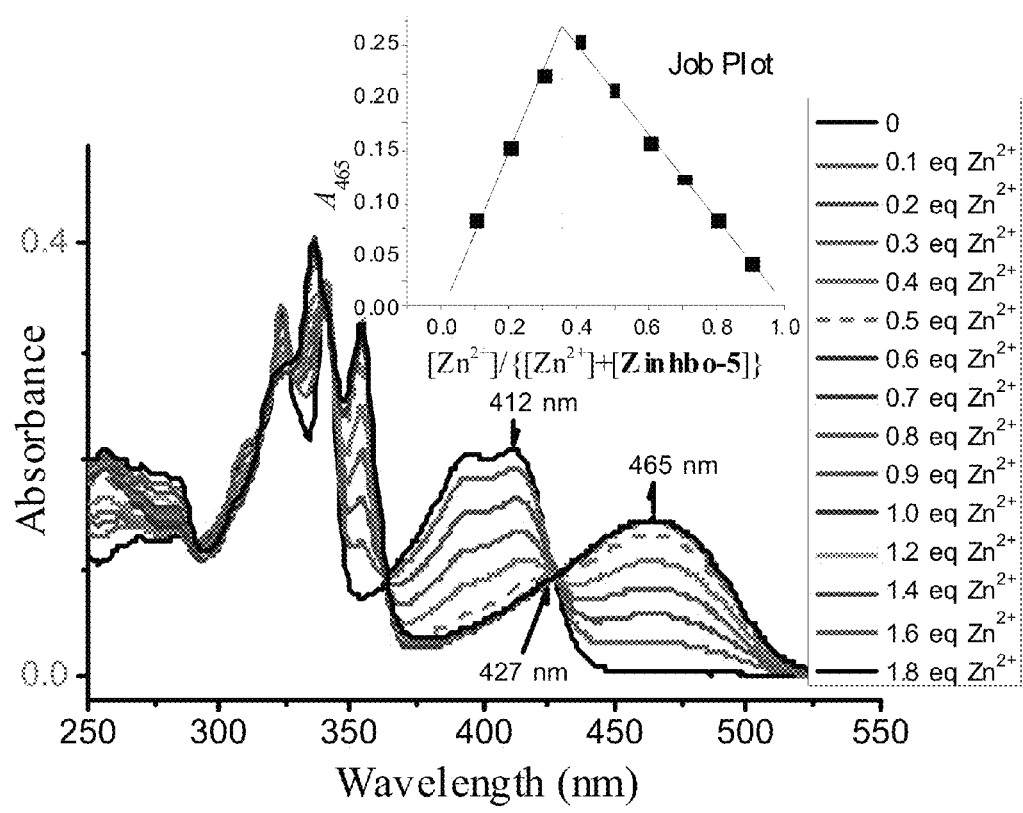
FIG. 7 provides a graph of the UV-vis spectra of an embodiment of the invention, Zinhbo-5 ($1.0 \times 10^{-5}$ M), in EtOH upon addition of zinc ions.
Figure 8:
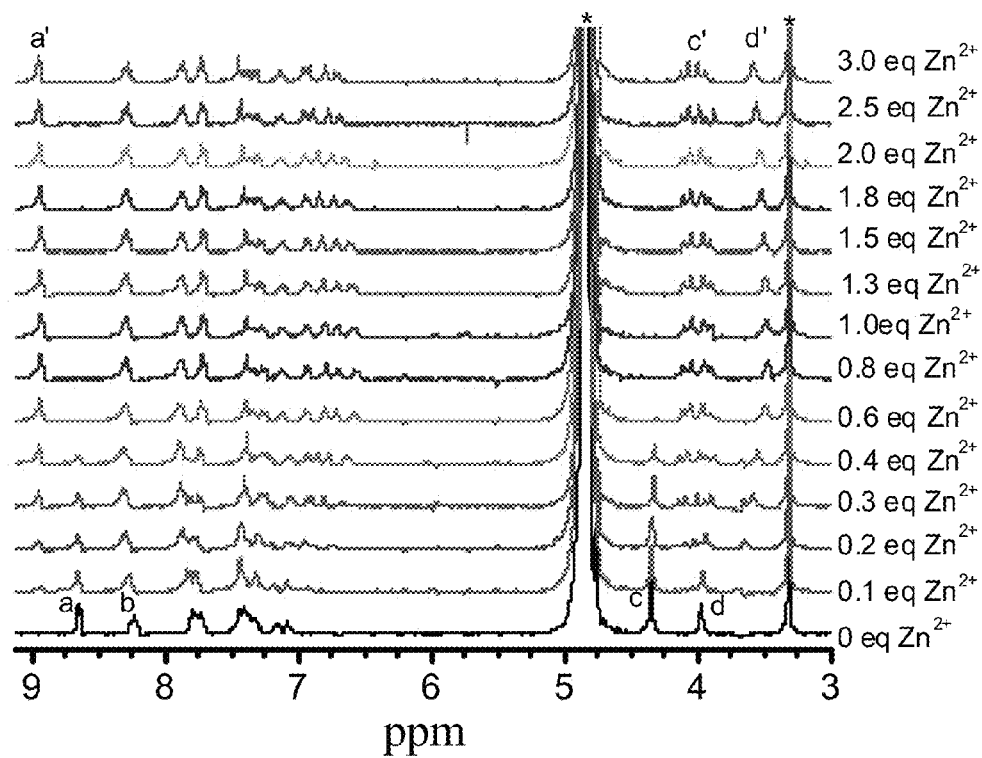
FIG. 8 provides a graph of a 300 MHz $^1$H NMR titration of Zinhbo-5 in $CD_3OD/D_2O$ (1:1, V/V) with $Zn(ClO_4)_2$. The t-butyl signal (as a singlet at 1.3 ppm) is not shown. The starred signals at 4.80 and 3.29 ppm are attributed to the $D_2O$ and $CD_3OD$ residues, respectively.
Figure 9:
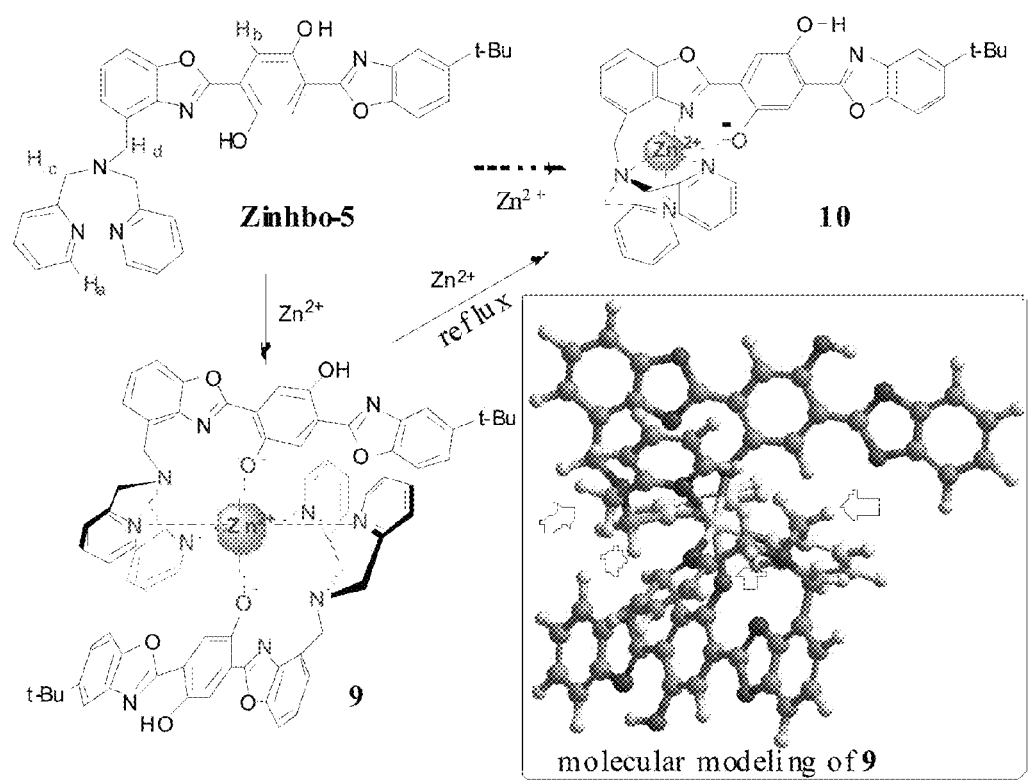
FIG. 9 provides a proposed metal complex formation from Zinhbo-5 and $Zn^{2+}$ cation. The inset of FIG. 9 shows the geometry-optimized structure for "(Zinhbo-5)$_2$-Zn" 9 (without t-butyl substituent, using HyperChem MM+). Two pyridyl groups on the back side are shown in the orange color for clarity. The thick arrows point to the methylene protons that become diastereotopic.

In ethanol, Zinhbo-5 exhibited an absorption band at ($\lambda_{max}$≈412 nm). Upon addition of Zn$^{2+}$, the absorption band was progressively decreased, which was accompanied with a new band at about 465 nm (FIG. 7). The large spectral bathochromic shift indicated the deprotonation, as a consequence of Zn$^{2+}$-binding to phenol. A clear isobestic point at about 427 nm suggested that Zn$^{2+}$-binding produced only one new chemical species. High resolution mass spectroscopy (HRMS) detected the mass 1409.238, corresponding to [2(Zinhbo-5)+ClO$_4$+Na+ Zn]+(the calcd mass for C$_{74}$H$_{65}$ClN$_{10}$O$_{12}$Zn: 1409.366). On the basis of Job plot and HRMS data, the reaction of Zinhbo-5 and Zn$^{2+}$ was assumed to give complex 9 with a ligand-to-metal ratio of 2:1 (FIG. 9). The ligand-to-metal ratio of 2:1 is also supported by titration experiment in $^1$H NMR (FIG. 8).

Figure 10:
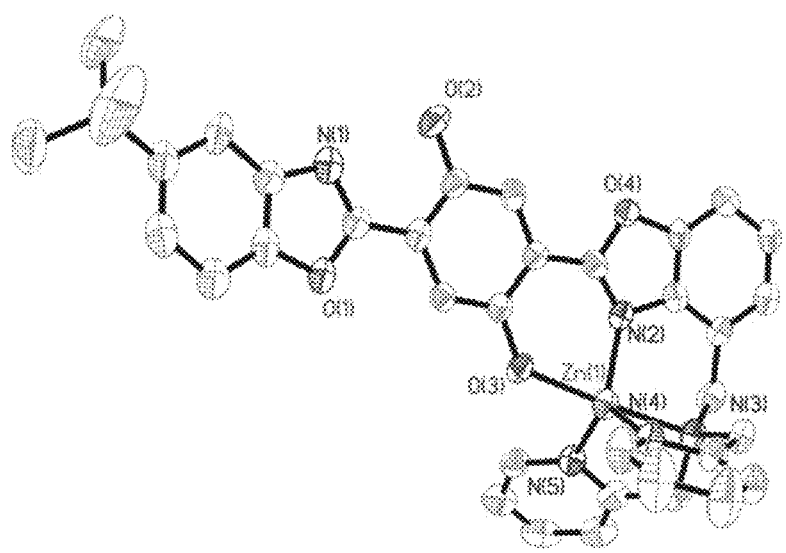
FIG. 10 provides a ORTEP plot of the crystal structure of Zinhbo-5-$Zn^{2+}$ (10) with the thermal ellipsoids drawn at 50% probability.

A mixture of Zinhbo-5 and Zn(ClO$_4$)$_2$ (1:1 molar ratio) in ethanol was refluxed for 10 min. After slow evaporation of solvent at room temperature, the product gave needle-like crystals. Crystal structure revealed the ligand-to-metal ratio of 1:1 (FIG. 10). Although a HBO derivative could have two possible rotamers that are interconvertible, the crystal 10 revealed only one, in which the free hydroxy group (labed as O(2) atom) was on the same side as the benzoxazole nitrogen N(1), thereby facilitating the desirable ESIPT. The structure showed that the Zn2+ cation was penta-coordinated. The crystal 10 gave a rather simple $^1$H NMR spectrum, revealing two methylene protons as singlets at 4.24 and 4.20 ppm (1:2 ratio) (FIG. 11), which is consistent with the reported Zinhbo-1-Zn$^{2+}$ complex.

Figure 11:
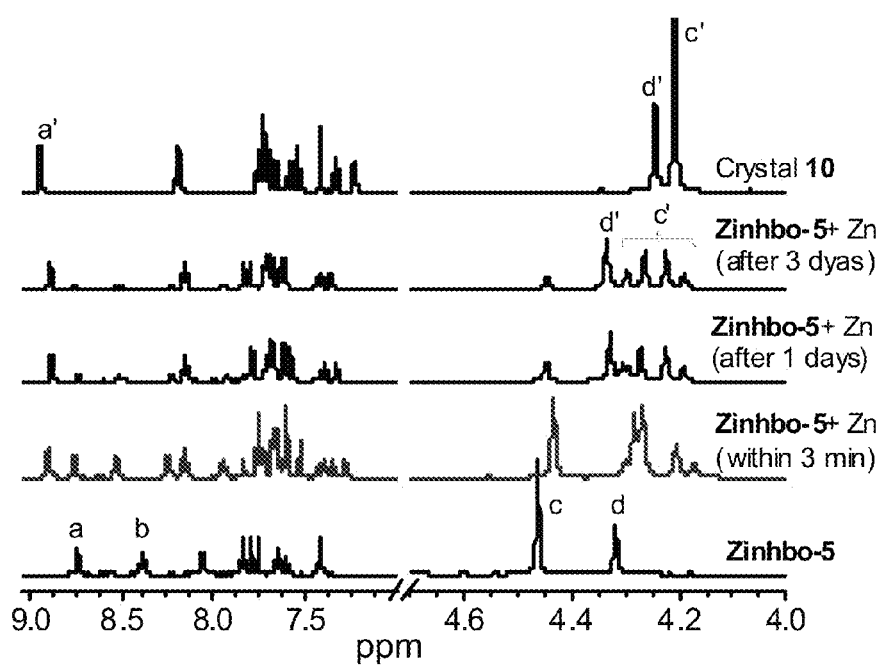
FIG. 11 provides a graph of a 500 MHz $^1$H NMR spectra of crystal 5 (first trace at the top) and "Zinhbo-5+$Zn^{2+}$ (1:1 molar ratio)" in $CD_3OD$. The descriptions in the parentheses indicates the time after mixing Zinhbo-5 with $Zn^{2+}$ cation. All spectra use $CD_3OD$ solvent signal at ~4.8 ppm (not shown) as reference.

The reaction of Zinhbo-5 and Zn$^{2+}$ (1:1 molar ratio) was further examined by $^1$H NMR at room temperature (FIG. 11). After addition of Zn$^{2+}$, the resonance signal at ~8.75 ppm (Ha) gradually disappeared as a consequence of zinc complexation. A quartet signal centered at ~4.24 ppm was clearly observed after mixing for 1 day, indicating the formation of complex 9. Part of the quartet signal could be seen when Zinhbo-5 and Zn$^{2+}$ were mixed for 3 minutes. After mixing for 3 days, no trace of complex 10 was observed, on the basis of chemical shifts for the singlet aromatic proton at 8.94 ppm (versus 8.89 ppm), and singlet methylene protons at 4.24 and 4.20 ppm. Therefore, mixing Zinhbo-5 with Zn$^{2+}$ gradually formed complex 9 as the kinetically favored product at room temperature, whose conversion to the thermodynamically more stable 10 can only occur at a higher temperature.

Fluorescence of Zinhbo-5-Zn$^{2+}$

Figure 12:
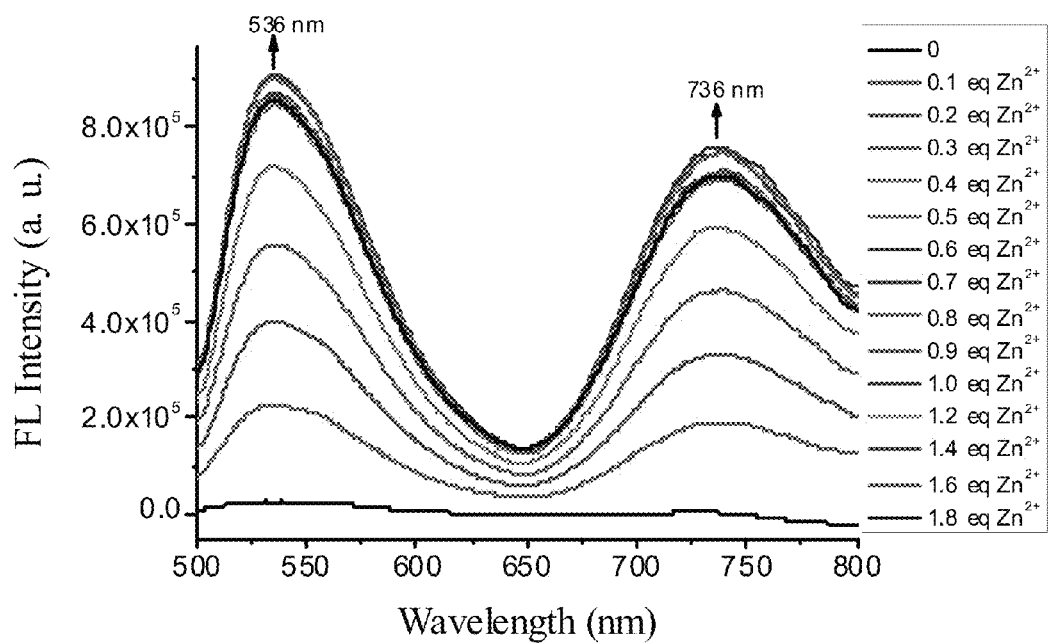
FIG. 12 provides a graph of the change in the fluorescence spectra for Zinhbo-5 ($1.0 \times 10^{-5}$ M) in EtOH with the addition of zinc ions.
Figure 13:
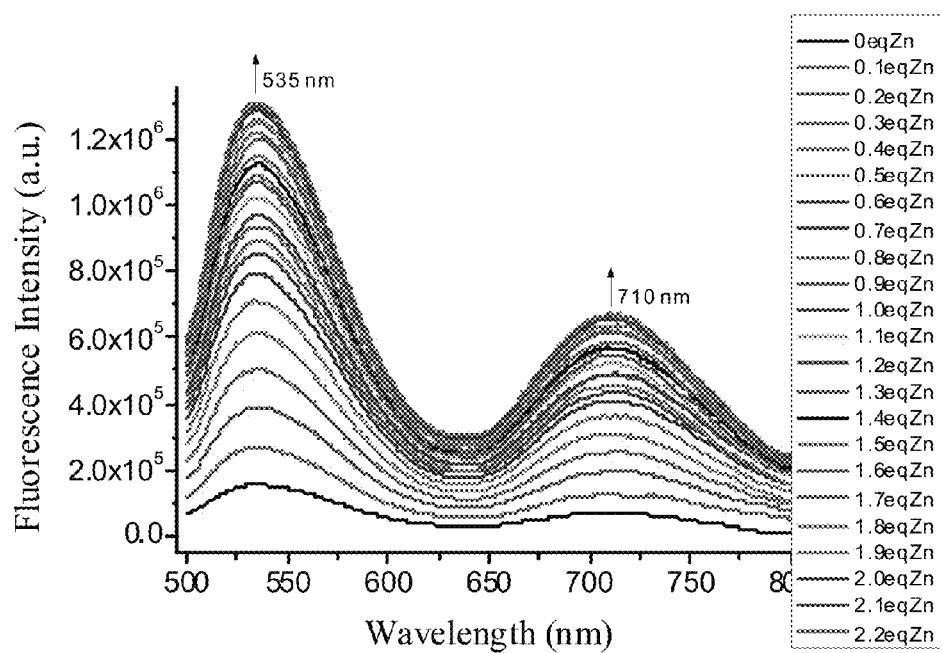
FIG. 13 provides a graph of the change in the emission spectra for Zinhbo-5 ($1.0 \times 10^{-5}$ M) in HEPES buffer solution containing 50% EtOH with the addition of zinc ions with excitation at 480 nm.
Figure 14:
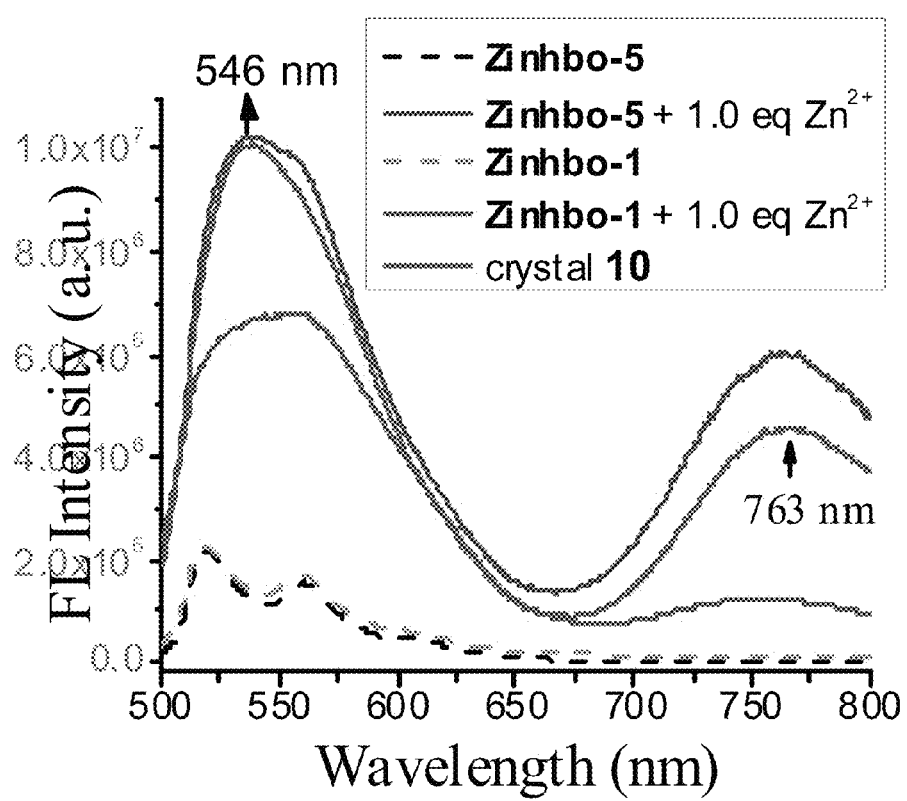
FIG. 14 provides the fluorescence spectra of Zinhbo-5 and Zinhbo-1 ($1.0 \times 10^{-5}$ M) upon addition of zinc cation in THF (excitation at 480 nm). (Zinhbo-5)$_2$-$Zn^{2+}$ (2:1 ligand-to-metal ratio) is the predominant form when $Zn^{2+}$ is added to Zinhbo-5 in solution.
Figure 15:
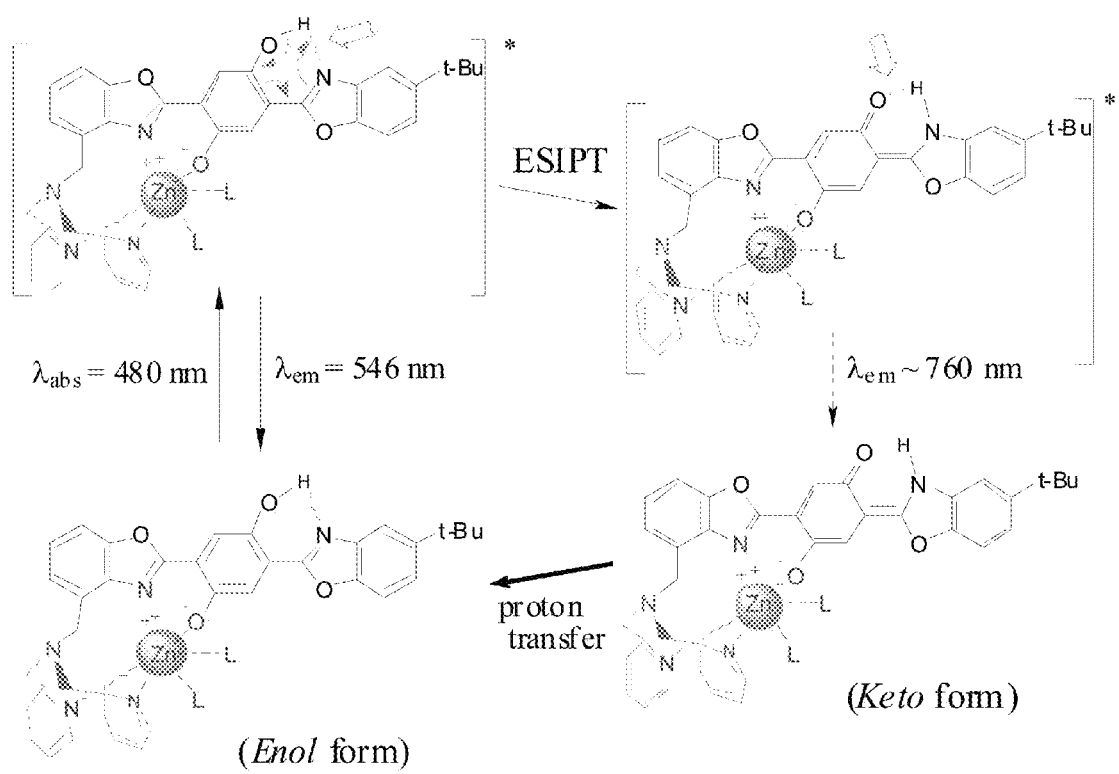
FIG. 15 provides a schematic representation of the ESIPT process of Zinhbo-5-Zn complex, involving the enol emission at 546 nm and keto emission at 763 nm. The thick arrows indicate the hydrogen bonds in the excited states.

Free ligand Zinhbo-5 gave only weak green fluorescence at 520 and 560 nm. The green fluorescence signal was increased gradually upon addition of Zn$^{2+}$ (FIGS. 12 and 13). In addition, a new emission peak at ~763 nm occurred, which has a very large Stokes shift (~285 nm). The new emission band was attributed to the keto form arising from the ESIPT process (FIGS. 14 and 15). Comparison between Zinhbo-5 and Zinhbo-1 showed that the former gave quite stronger NIR emission (at ~763 nm) upon zinc binding (FIG. 14). The stronger NIR emission (at ~763 nm) from Zinhbo-5 indicated that the keto emission, enabled through zinc binding, is quite sensitive to the substitution position. This is because the substituent at the 5-position of benzoxazole unit exerts less electronic interferences to the anticipated ESIPT process (as shown in structure 5). Interestingly, the desirable NIR emission was also affected by the complex structure. The NIR emission band (at 763 nm) from the simple mixing of Zinhbo-5 with Zn$^{2+"}$, which gave predominant 9, was noticeably stronger than that from the crystal 10 with well defined 1:1 ratio of Zinhbo-5 to Zn$^{2+}$ ion. The stronger ESIPT from 9 could be associated with the increased rigidity, when two ligands were assembled together via chelation with Zn$^{2+}$ cation.

Figure 16:
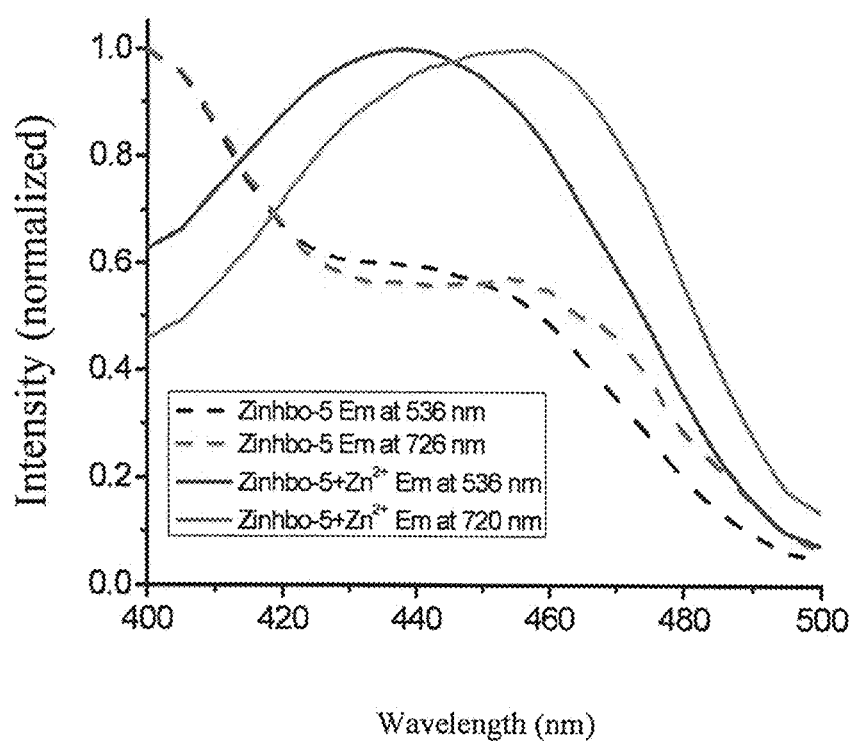
FIG. 16 provides a graph of the excitation spectra for Zinhbo-5 ($1.0 \times 10^{-5}$ M) in HEPES buffer solution containing 50% EtOH with and without 1 equivalent of zinc ions.

Excitation spectra of Zinhbo-5+Zn$^{2+}$ in THF was monitored at 526 and 720 nm (FIG. 16). The excitation maximum of Zinhbo-5+Zn$^{2+}$ revealed peaks at ~460 nm, corresponding to the absorption $\lambda_{max}$ of the deprotonated Zinhbo-5 in the complex. The result indicated that the emission signals at ~540 and ~770 nm were originated from the same species, i.e. Zinhbo-5-Zn$^{2+}$ complex, that gave both enol and keto emission.

Figure 17:
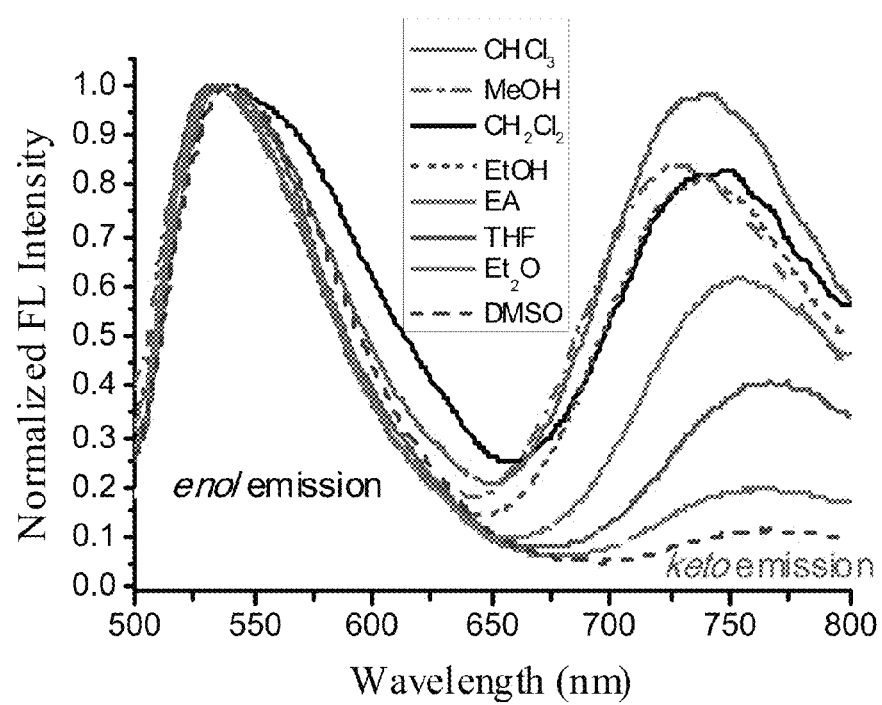
FIG. 17 provides the fluorescence spectra for Zinhbo-5 ($1.0 \times 10^{-5}$ M) in different solvents with 1 equivalent of zinc ions.

The keto emission of Zinhbo-5-Zn$^{2+}$ complex was quite responsive to solvent polarity (FIG. 17). Non-polar solvents such as ether appeared to disfavor the ESIPT. In DMSO (a polar aprotic solvent), Zn$^{2+}$ could be solvated to reduce the metal binding to phenoxide, thereby inhibiting the ESIPT. Interestingly, the ESIPT signals were stronger in the protic solvents (EtOH and MeOH). A possible rational is that protic solvents interacted with phenoxide by hydrogen bonding, thereby further reducing the negative charge impact of the phenoxide oxygen and enhancing the ESIPT.

Figure 18:
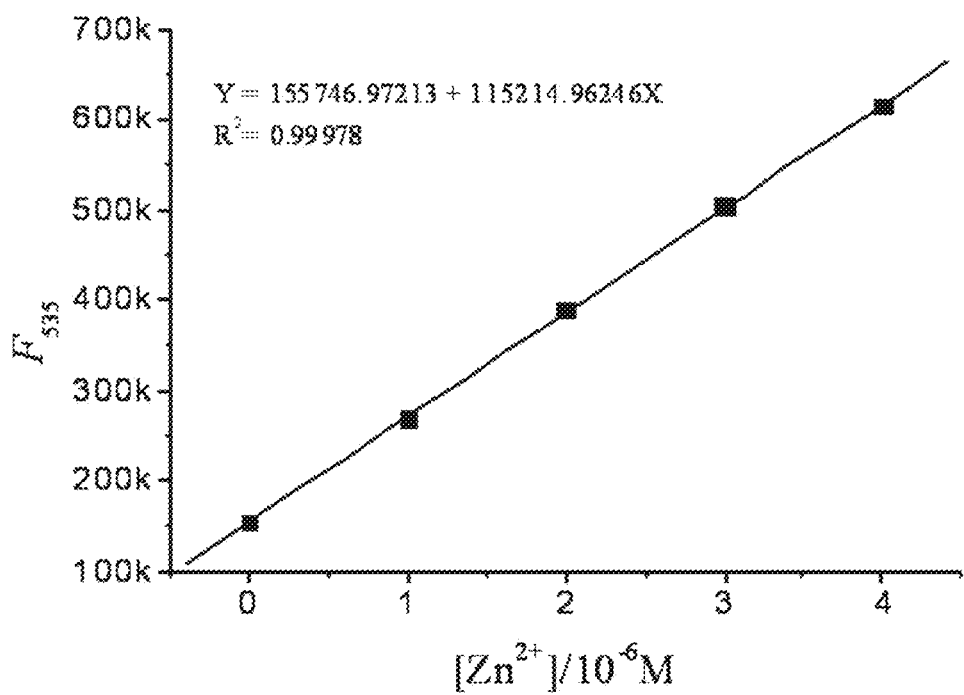
FIG. 18 provides a graph of the fluorescence intensity of Zinhbo-5 (10 µM) at 535 nm as a function of concentration of $Zn^{2+}$ (0-4 µM) in $H_2O$/EtOH (5/5) solution (containing 50 M HEPES, 0.1M $KNO_3$, pH=7.2). The inset of FIG. 18 provides the emission spectra of Zinhbo-5 in the presence of different concentrations of $Zn^{2+}$ ion. The linearly dependent coefficient is: $R^2$=0.99978.
Figure 19:
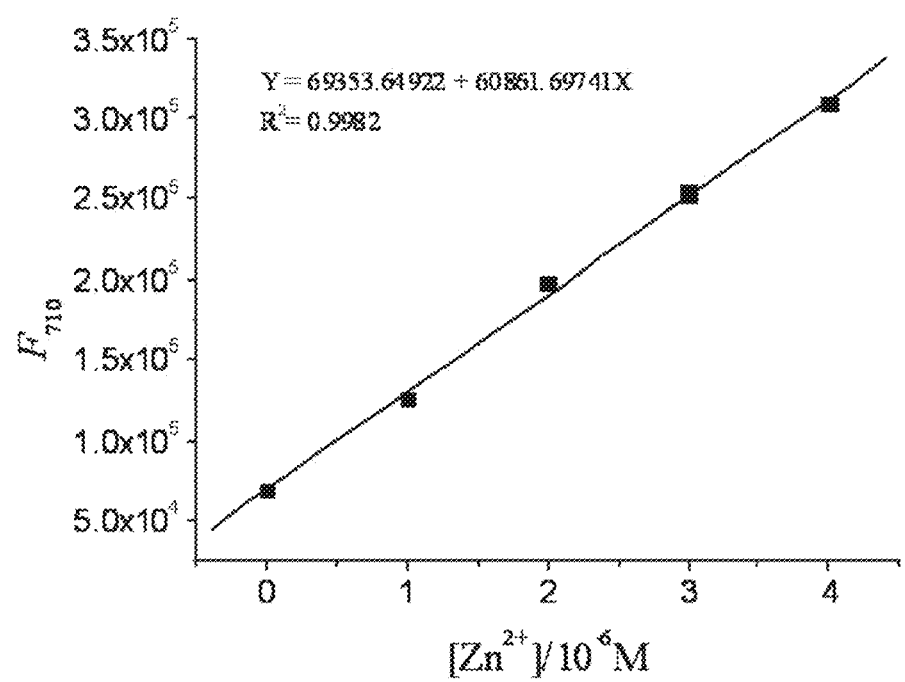
FIG. 19 provides a graph of the fluorescence intensity of Zinhbo-5 (10 µM) at 710 nm as a function of concentration of $Zn^{2+}$ (0-4 µM) in $H_2O$/EtOH (5/5) solution (containing 50 M HEPES, 0.1M $KNO_3$, pH=7.2). The inset of FIG. 19 provides the emission spectra of Zinhbo-5 in the presence of different concentrations of $Zn^{2+}$ ion. The linearly dependent coefficient is: $R^2$=0.9982.

In HEPES buffer solution with 50% EtOH, the weak fluorescence of free ligand Zinhbo-5 ($\Phi_{fl}$=0.081) was increased notably to $\Phi_{fl}$=0.17, upon addition of one equivalent Zn2+ cation. The NIR emission intensity at ~710 nm was linearly proportional to the $Zn^{2+}$ concentration (linearly dependent coefficient: $R^2$=0.9982) (FIGS. 18 and 19). The result indicated that sensor Zinhbo-5 could be potentially useful for quantitative detection of $Zn^{2+}$ concentration. The association constants $K_{11}$ and $K_{12}$ were determined by a nonlinear least-squares analysis of fluorescence intensity versus $Zn^{2+}$ ion concentration to be $3.21 \times 10^5$ $M^{-1}$ and $3.88 \times 10^{10}$ $M^{-2}$, respectively.

Potential Use in Zinc Imaging
Detection of Intracellular $Zn^{2+}$ with Zinhbo-5

Figure 20:
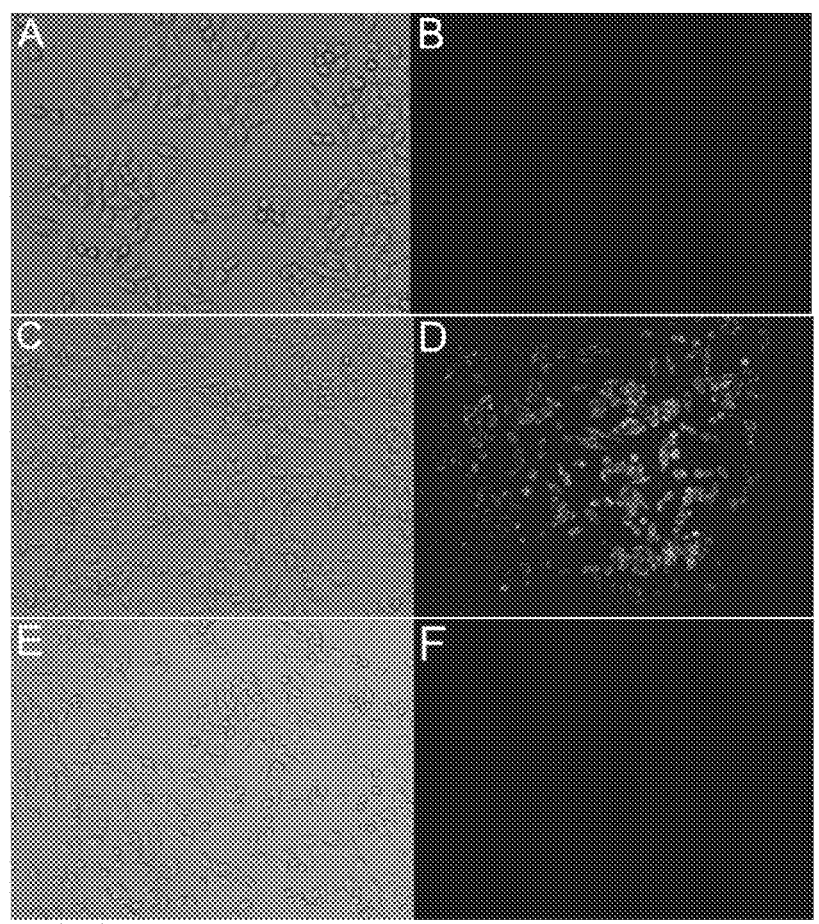
FIG. 20 provides the fluorescence images of Hela cells incubated with 10 µM Zinhbo-5 for 30 min (b) and then further incubated with 20 µM $Zn^{2+}$ for 30 min (d) and then subsequent addition of 2 mM TPEN (f). The bright-field transmission image of cells corresponding to their images are: (a, c, e; a→b, c→d, e→f).

The Zinhbo-5 sensor was applied on Hela cells, in order to examine whether the probe could be useful in living systems under a confocal laser scanning microscopy. Cultured Hela cells were incubated with Zinhbo-5 in culture medium for 30 min at 37° C., and very weak fluorescence of Zinhbo-5 inside the living Hela cells was observed. After three times washing with PBS buffer, the cells were incubated with $ZnCl_2$ (10 μM) in the medium for another 30 min at 37° C., and the fluorescence in living cells was much brighter (FIG. 20, at D). A bright-field transmission image of cells treated with Zinhbo-5 and $Zn^{2+}$ confirmed that the cells were viable throughout the imaging experiments (FIG. 20, at C). Subsequent addition of the high-affinity zinc chelator N,N,N',N'-tetrakis(2-pyridylmethyl)ethylenediamine (TPEN) reverted the emission intensity to that of the zinc-free system (FIG. 20, at F). Zinhbo-5 can also be applied to MCF-7 breast cancer cell, giving the similar results. The results demonstrated that Zinhbo-5 was cell-permeable and primarily nontoxic to the cell culture and useful for the imaging of $Zn^{2+}$ in living cells.

Imaging of $Zn^{2+}$ in Zebrafish

Figure 21:
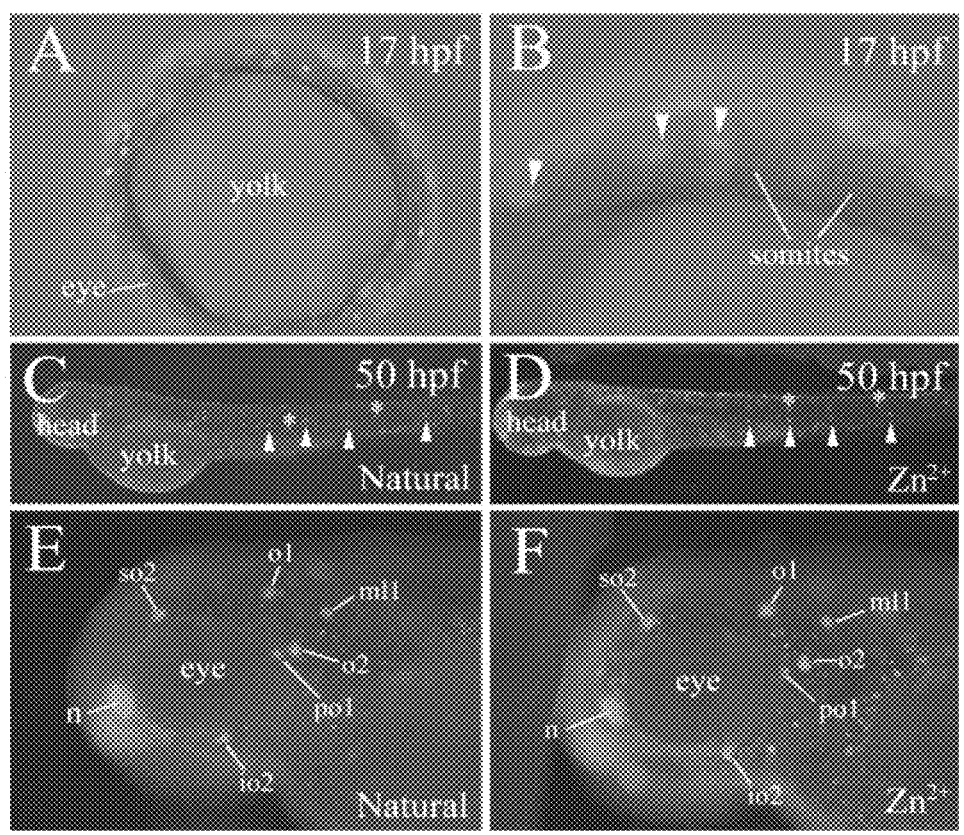
FIG. 21 provides Zinhbo-5 labeling of developing zebrafish at 17 and 50 hours post fertilization (hpf).
Figure 22:
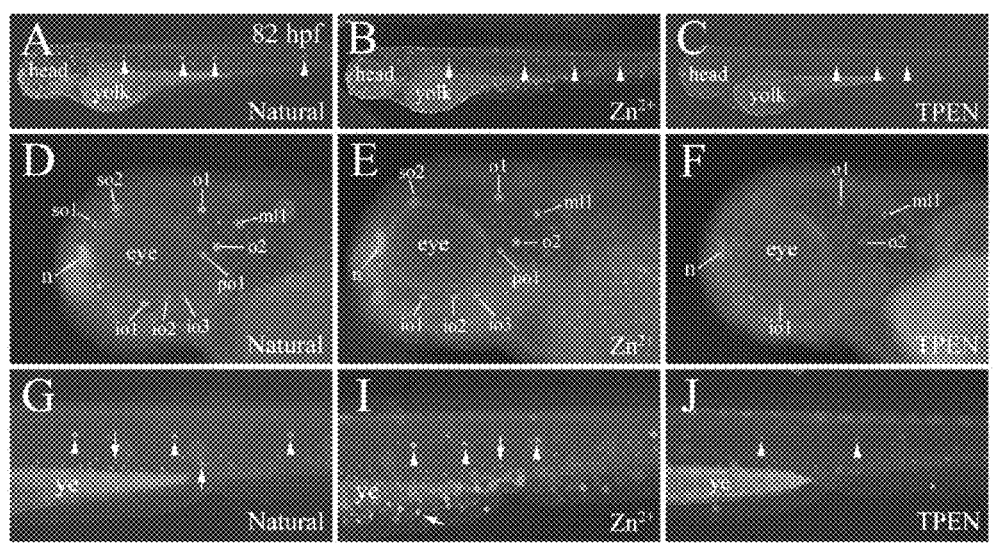
FIG. 22 provides that Zinhbo-5 labeling is greatly reduced in zebrafish larvae (82 hpf) exposed to TPEN, which is a zinc chelator.

The most attractive application for zinc probes is sensing $Zn^{2+}$ in living organisms. Our ability to discover the fundamental roles of $Zn^{2+}$ is dependent on the tools available to detect the $Zn^{2+}$ population/concentration in living biological systems. Zebrafish has recently become an important model organism for the study of vertebrate imaging. This is because the embryos of zebrafish are transparent, allowing for clear observation of their organs without the need for dissection. The optical transparancy of zebrafish, therefore, provides a convenient organism for detection of ions by fluorescence microscopy. Several studies have demonstrated the wide use of zebrafish in detecting $Zn^{2+}$ ions. Encouraged by the cell permeability (FIG. 20), Zinhbo-5 was thus examined in developing zebrafish of various stages by adding Zinhbo-5 to fish tank water (treatment lasted for one hour at room temperature). At 17 hours post fertilization (hpf), the zinc-concentrated cells appeared as green spots which were distributed throughout the embryos (FIG. 21, at A and B). At 50 hpf (FIG. 21, at C-F) and 72 hpf (data not shown), the zinc-concentrated cells are mainly located in the nose and neuromasts of the lateral line system, similar to expression of MTF-1, a zinc finger protein, in zebrafish embryos. The Zinhbo-5 labeling pattern remained similar in older larvae (82 hpf, FIG. 22, at A and D). Zinhbo-5 labeling was almost completely eliminated in 82 hpf larvae treated with TPEN, a zinc chelator (FIG. 22, at C, F and J), confirming that the observed Zinhbo-5 labeling was indeed correlated to the presence of $Zn^{2+}$ ion. There was no obvious difference in Zinhbo-5 labeling in the lateral line structures between larvae treated with exogenous $Zn^{2+}$ (20 μM, FIG. 22, at B, E and I) and untreated larvae (FIG. 22, at A, D and G), suggesting that the fluorescence-spotted area resulted from endogeneous zinc ions in fish and not from sequestration of the probe. However, there were more labeling in other parts of the body in the $Zn^{2+}$ treated larvae (FIG. 22 at I). Although several studies have demonstrated the use of zebrafish in detecting $Zn^{2+}$ ions, the exact organ associated with the $Zn^{2+}$ bright dots is not known yet. Herein the in vivo recognition of the zinc-rich organ in zebrafish larva could be seen with higher image quality by using Zinhbo-5. All the results suggest that Zinhbo-5 has the potential to become a useful sensor for tracing the $Zn^{2+}$ storage in the specific organs during the development of zebrafish. The in vivo results with sensor Zinhbo-5 are somewhat different in light of the previously reported data where zinc was detected using fluorescent sensors in zebrafish. In those studies, fluorescent labeling was concentrated in the heart ventricle of embryos (50 hpf), and scattered throughout the body in larvae (4-5-day old). Whereas Zinhbo-5 labeling is confined mainly to the nose and neuromasts of the lateral line system during this period.

FIG. 21: Zinhbo-5 Labeling of Developing Zebrafish at 17 and 50 Hours Post Fertilization (hpf).

All images show lateral views of live embryos (anterior to the left and dorsal up). The labeled cells are scattered throughout the embryo at 17 hpf (panels A and B). Panel B is a higher magnification of the mid-trunk region of the embryo shown in panel A. Arrowheads in panel B indicate several labeled cells. Zinhbo-5 labeling becomes more restricted as development proceeds. At 50 hpf, Most labeled cells are concentrated in the nose neuromasts of the lateral line system (panels C-F). Arrowheads and asterisks in panels C and D point to some neuromasts in the posterior lateral line system on this side and the other side of the body trunk, respectively. Panels E and F are higher magnifications of the head region of the labeled embryos. Embryos in panels D and F had been treated with Zn2+ before Zinhbo-5 labeling. (Abbreviations: io2, infraorbital line neuromast 2; ml1, middle line neuromast 1; n, nose; o1 and o2, otic lateral line neuromasts 1 and 2; po1, postorbital neuromast 1; so2, supraorbital line neuromast 2).

FIG. 22

Zinhbo-5 labeling is greatly reduced in zebrafish larvae (82 hpf) exposed to TPEN, a zinc chelator. All images show lateral views (anterior to the left and dorsal up) of live zebrafish larvae. Panels A-C are low magnification images showing almost the entire fish; panels D-F show higher magnification of the head region, while panels G-J show higher magnification of the mid-trunk region of the fish. Panels A, D and G are from larvae labeled with Zinhbo-5. Panels B, E and I are from larvae that had been treated with zinc before exposed to Zinhbo-5. Panels C, F and J are from larvae that were simultaneously treated with Zinhbo-5 and TPEN. Arrowheads point to some labeled neuromasts, while arrows indicate a few labeled cells that do not belong to the lateral line system. (Abbreviations: io1 and io3, infraorbital line neuromasts 1 and 3; so1, supraorbital line neuromast 1; ye, yolk extension. Other abbreviations are the same as in FIG. 9).

Conclusion

We have designed and synthesized Zinhbo-5, in which a tert-butyl group was introduced to perturb the optical behaviors of bis(benzoxazole) chromophore. Selective $Zn^{2+}$-binding enables the mechanism for excited state intramolecular proton transfer, thereby leading to NIR emission (~710-760 nm) with a large Stokes shift (240 nm). With the aid of spectroscopic studies, the stoichiometry between Zinhbo-5 and $Zn^{2+}$ is found to be 2:1 in the initially formed complex.

The complex of 2(Zinhbo-5).$Zn^{2+}$, however, can be transformed into thermodynamically more stable Zinhbo-5.$Zn^{2+}$ (with 1:1 ligand to metal ratio). At ambient temperature, Zinhbo-5+$Zn^{2+}$ complex gives two emission bands (about 546 & 710 nm) in aqueous solution, allowing detection by using both visible and NIR microscopy. The probe can easily penetrate through cell membranes for in vivo applications. The Zinhbo-5 can also be applied to detect zinc ions during the development of living zebrafish embryos. In comparison with the known zinc sensors for zebrafish, the developed probe shows selective recognition of neuromast region, suggesting that the new probes might be able to recognize the zinc in certain regions over the others. The develop probe thus could provide a potentially useful tool for monitoring the distribution of $Zn^{2+}$ in biology.

Experimental Section

Materials and General Procedure

All the solvents were of analytic grade. The salt used in stock solutions of metal ions were $Zn(OAc)_2.2H_2O$, $Co(OAc)_2.4H_2O$, $Ni(OAc)_2.4H_2O$, $Cu(OAc)_2.H_2O$, $MgSO_4$, $Cd(OAc)_2.6H_2O$, $Mn(OAc)_2.4H_2O$, $FeCl_2.4H_2O$, $CaCl_2$, $Na_2SO_4$, $Hg(OAc)_2$, $AgNO_3$, $Pb(OAc)_2.3H_2O$, $KNO_3$. Water used was ultra filter deionized and purchased from fisher. HEPES (2-[4-(2-hydroxyethyl)-1-piperazinyl]-ethanesulfonic acid) was from Fisher. NMR spectra were collected on a Varian 300 Gemini spectrometer. Mass spectrometric data were obtained on a HP1100LC/MSD mass spectrometry. UV-Vis spectra were acquired on a Hewlett-Packard 8453 diode-array spectrometer. Fluorescence spectra were obtained on a HORIBA Jobin Yvon NanoLog spectrometer. All pH measurements were made with a model RS232 meter. The fluorescence quantum yield were obtained using quinine sulfate as the standard ($\Phi$=0.53, 0.1M $H_2SO_4$). Cell fluorescence imaging were obtained on a Nikon Eclipse TE2000-5 fluorescence microscope, and analyzed by MetaFluor software (Universal Imaging Corp.).

Determination of Association Constant

An approximate linear fit formula is used to calculate the single association constant $K_{ass1}$ and $K_{ass2}$:

$$\frac{1}{n}\frac{F-F_0}{F_1-F} = \frac{2k_1 K_{ass2} C_0}{F_1-F_0}(F_1-F) + K_{ass1} C_0$$

where n is the number of equivalents of the added metal ions, $F_0$ is the fluorescence intensity of the free sensor, and $F_1$ is the fluorescence intensity in the presence of excess cation, $C_0$ is the initial concentration of Zinhbo-5. $K_{ass1}$ and $K_{ass2}$ can be obtained by a linear analysis of $$(F_1-F)(x)$$

versus $$\frac{1}{n}\frac{F-F_0}{F_1-F}(y).$$

The individual profile of the fluorescence at 710 nm demonstrated a 2:1 stoichiometric host-guest complex for Zinhbo-5 and $Zn^{2+}$, with the overall association constant being calculated as Kass=3.88×10$^{10}$ M$^{-2}$ (Kass1=3.21×10$^5$ M$^{-1}$, Kass2=1.21×10$^5$ M$^{-1}$, respectively).

Experimental Details for the Cell Imaging Experiments

Hela cells were cultured in DEME (Invitrogen) supplemented with 10% FCS (Invitrogen). One day before imaging, cells were seeded in 24-well flat-bottomed plates. The next day, the Hela cells were incubated with 10 μM sensor Zinhbo-5 for 0.5 h at 37° C. under 5% $CO_2$ and then washed with phosphate-buffered saline (PBS) three times before incubating with 10 μM $ZnCl_2$ for another 0.5 h, cells were rinsed with PBS three times again, then the fluorescence imaging of intracelluar Zn2+ was observed under Nikon eclipse TE2000-5 inverted fluorescence microscopy with a 32× objective lens. The Hela cells only incubated with 10 μM Zinhbo-5 for 0.5 hour at 37° C. under 5% $CO_2$ was as a control. For all images, the microscope settings, such as brightness, contrast, and exposure time were held constant to compare the relative intensity of intracellular $Zn^{2+}$ fluorescence.

Experimental Procedure for Synthesis of Zinhbo-5

2-(4-methylbenzoxazolyl)-5-(hydroxylmethyl)-1,4-bis(hexyloxy)benzene

The sensor Zinhbo-5 can be synthesized as shown in Scheme 1, which requires a sequential construction of two benzoxazole units. The first benzoxazole unit is constructed by reaction of 2-amino-m-cresol with 2,5-bis(hexyloxy)-4-(hydroxymethyl)benzaldehyde in three steps (in 71% yield). The second benzoxazole unit is synthesized by reaction of 2-amino-4-(tert-butyl)phenol with 4-(4-methylbenzoxazolyl)-2,5-bis(hexyloxy)benzaldehyde.

Scheme 1. Synthesis of Zinhbo-5 sensor.

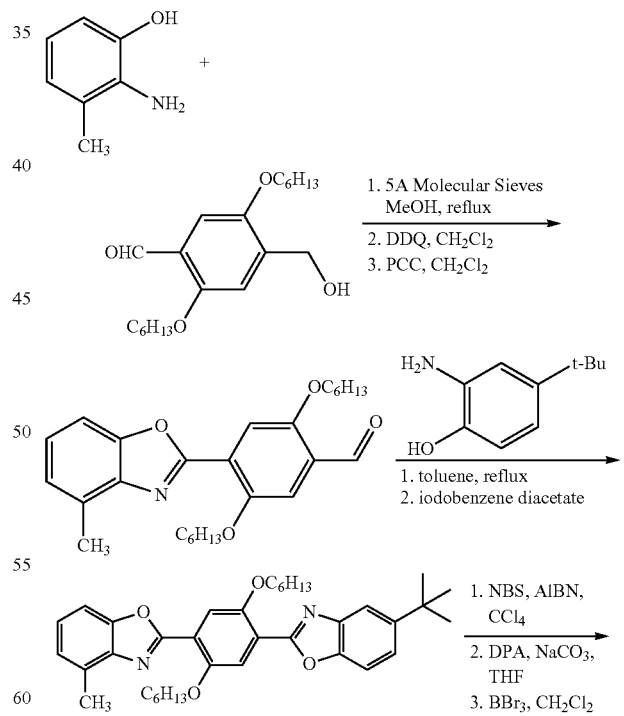

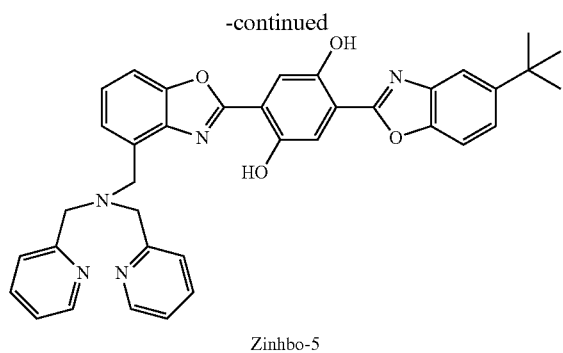

Zinhbo-5

Herein, the detailed synthetic procedure is described to illustrate the features related to the compound preparations, chemical synthesis, and spectroscopic properties. For the first reaction shown in Scheme 1, activated molecular sieves (5 Å) was added to 100 mL MeOH in 500 mL flask. Into this flask were charged 2-amino-m-cresol (2.39 g, 21.7 mmol) and 2,5-bis(hexyloxy)-4-(hydroxymethyl)benzaldehyde (2.54 g, 21.7 mmol). The resulting mixture solution was heated to reflux overnight. The solution was cooled to room temperature, filtered, and solvent was removed using a rotary evaporator. Then solution of DDQ (2,3-dichloro-5,6-dicyano-1,4-benzoquinone) (4.85 g, 21.4 mmol) in 700 mL $CH_2Cl_2$ was added to the above residue. After stirring at room temperature for 2 h, the reaction mixture was treated with 400 mL saturated $Na_2CO_3$ and methyl chloride to remove the DDQH by-product, then washed with water and brine, and dried over $Na_2SO_4$. After evaporation of the solvent, the solid residues were collected and purified on a silica gel column by using an eluant (hexane:$CH_3COOEt$=15:1). After recrystallization from methanol, the product 2-(4-methylbenzoxazolyl)-5-(hydroxylmethyl)-1,4-bis(hexyloxy)benzene was obtained as an off-white solid (7.8 g, 81.8%), which has the following spectral properties. $^1$H NMR (CDCl$_3$, 300 MHz, δ): 7.58 (s, 1H), 7.39 (d, J=8.4 Hz, 1H), 7.32 (dd, J=8.4 Hz, J=8.1 Hz, 1H), 7.14 (d, J=7.5 Hz, 1H), 7.06 (s, 1H), 4.74 (d, J=6.6 Hz, 2H), 4.07 (tt, J=6.3 Hz, 4H), 2.68 (s, 3H), 1.83 (m, 4H), 1.58 (m, 4H), 1.34 (m, 8H), 0.89 (m, 6H). MS (EI): [M+H$^+$]$^+$ =356.3, [M+Na$^+$]$^+$=462.3.

A solution of 2-(4-methylbenzoxazolyl)-5-(hydroxylmethyl)-1,4-bis(hexyloxy)benzene (1.99 g, 4.53 mmol) in $CH_2Cl_2$ (10 mL) was added dropwise to a stirred solution of freshly prepared pyridium chlorochromate (PCC) (1.46 g, 6.80 mmol) in $CH_2Cl_2$ (100 mL) at room temperature. Anhydrous Et$_2$O (100 mL) was added, and the mixture was stirred for an additional 2 h. The reaction mixture was then directly transferred onto the top of a short silica gel column. The yellow and highly fluorescent product was then washed off the column with $CH_2Cl_2$, giving 2,5-bis(hexyloxy)-4-(hydroxymethyl)benzaldehyde in 86.9% (1.72 g). The product (mp. 48-50° C.) had the following spectral properties. $^1$H NMR (CDCl$_3$, 300 MHz, δ): 10.53 (s, 1H, —CHO), 7.78 (s, 1H), 7.48 (s, 1H), 7.40 (d, J=8.4 Hz, 1H), 7.26 (dd, J=7.8 Hz, J=7.8 Hz, 1H), 7.17 (d, J=7.2 Hz, 1H), 4.18 (t, J=6.6 Hz, 2H), 4.12 (t, J=6.0 Hz, 2H), 2.68 (s, 3H), 1.87 (q, J=6.3 Hz, 4H), 1.54 (m, 4H), 1.35 (m, 8H), 0.90 (m, 6H). IR(KBr): 1684 cm$^{-1}$, 1609.5 cm$^{-1}$, 1534.6 cm$^{-1}$.

2,5-Bis(hexyloxy)-4-(hydroxymethyl)benzaldehyde (4.3 g, 9.8 mmol) and 2-amino-4-tert-butylphenol (1.79 g, 10 mmol) were heated to reflux in toluene (30 mL) under an argon atmosphere for 15 h. The solvent was removed, MeOH/ $CH_2Cl_2$ (1:1) (200 mL) and iodobenzene diacetate (3.22 g. 10 mmol) were added subsequently. The resulting mixture was stirred at room temperature for 1 h. After removing solvent under reduced pressure, the residue was neutralized with aqueous sodium bicarbonate solution. After extraction with $CH_2Cl_2$ and purification on a silica gel column, the product 2-(2,5-bis(hexyloxy)-4-(4-methylbenzo[d]oxazol-2-yl)phenyl)-5-(tert-butyl)benzo[d]oxazol was obtained (3.7 g, 64.6%). $^1$H NMR (CDCl$_3$, 300 MHz, δ): 7.86 (s, 2H), 7.84 (s, 1H), 7.49 (d, J=8.4 Hz, 1H), 7.45 (s, 1H), 7.40 (d, J=7.2 Hz, 1H), 7.25 (dd, J=7.8 Hz, J=7.8 Hz, 1H), 7.15 (d, J=7.5 Hz, 1H), 4.21 (tt, J=6.3 Hz, 4H), 2.69 (s, 3H), 1.96-1.86 (m, 4H), 1.63-1.55 (m, 4H), 1.40 (s, 9H), 1.38-1.33 (m, 8H), 0.93-0.87 (m, 6H). $^{13}$C NMR (CDCl$_3$, 75 MHz, δ ppm): 169.50, 161.84, 160.56, 152.07, 152.04, 152.02, 150.68, 149.13, 148.18, 141.90, 141.44, 139.65, 130.87, 125.19, 123.22, 120.21, 120.03, 116.75, 116.54, 116.31, 109.95, 108.01, 94.81, 70.29, 51.84, 37.80, 35.14, 31.90, 29.60, 28.77, 26.98, 22.90, 16.77, 14.30. HRMS (ESI+) m/z: (M+H)$^+$ calcd for $C_{37}H_{47}N_2O_4$, 583.3536. found: 583.3540.

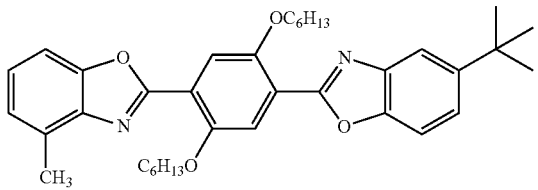

A mixture of 2-(2,5-bis(hexyloxy)-4-(4-methylbenzo[d] oxazol-2-yl)phenyl)-5-(tert-butyl)benzo[d]oxazol (3.7 g, 6.35 mmol), N-bromosuccinimide (NBS) (1.13 g, 6.35 mmol), and AIBN (0.1 g, 0.6 mmol) in CCl$_4$ (40 mL) was heated to reflux for 15 h under dry argon atmosphere. The reaction mixture was cooled to 0° C. and the precipitate was removed by filtration while maintaining the temperature at 0° C. After the solvent was evaporated, 4-(bromomethyl)-2-(4-(5-(tert-butyl)benzo[d]oxazol-2-yl)-2,5-bis(hexyloxy)phenyl)benzo[d]oxazole was obtained as an oil, which was used for next step without further purification.

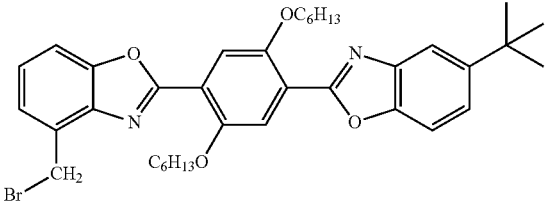

A mixture of 4-(bromomethyl)-2-(4-(5-(tert-butyl)benzo [d]oxazol-2-yl)-2,5-bis(hexyloxy)phenyl)benzo[d]oxazole (4.2 g, 6.35 mol), di-2-picolylamine (DPA) (3.78 g, 190 mmol), and Na$_2$CO$_3$ (6.73 g, 630 mmol) in dry THF (30 mL) was refluxed overnight. The resulting mixture solution was cooled to room temperature and the solvent was removed, water (50 mL) was added to the residues, followed by extraction with $CH_2Cl_2$. The combined organic phase was washed with brine, dried over MgSO$_4$, and concentrated on a rotatory evaporator. After purification on a silica gel column, the product was obtained as a yellow oil (0.6 g, 12.1%). $^1$H NMR (CDCl$_3$, 300 MHz, δ): 8.36 (d, J=4.8 Hz, 2H), 7.76 (d, J=6.3 Hz, 2H), 7.72 (s, 2H), 7.61 (d, J=8.1 Hz, 2H), 7.48 (dd, J=6.9 Hz, J=7.2 Hz, 2H), 7.36-7.22 (m, 2H), 6.98-6.97 (m, 4H), 4.13 (s, 2H), 4.06 (m, 4H), 3.83 (s, 4H), 1.96-1.86 (m, 4H), 1.75 (m, 4H), 1.46 (m, 4H), 1.25 (s, 9H), 1.21 (m, 8H), 0.75

(m, 6H). $^{13}$C NMR (CDCl$_3$, 75 MHz, δ ppm): 177.71, 173.49, 158.38, 150.13, 149.03, 141.32, 136.56, 131.19, 122.05, 120.16, 116.66, 109.22, 93.68, 70.14, 67.72, 64.58, 60.33, 59.71, 54.22, 53.36, 51.55, 38.50, 35.05, 31.92, 31.70, 29.45, 27.70, 25.85, 22.79, 14.26. HRMS (ESI+) m/z: (M+H)±calcd for C$_{34}$H$_{27}$N$_5$O$_4$, 780.4489. found: 780.4483.

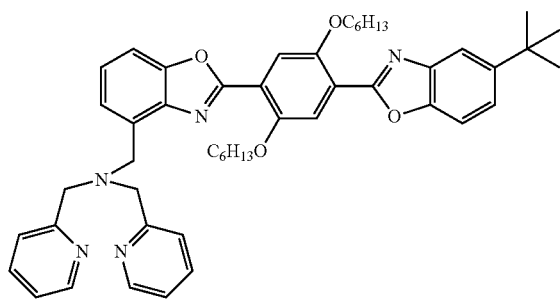

A solution of 1-(2-(4-(5-(tert-butyl)benzo[d]oxazol-2-yl)-2,5-bis(hexyloxy)phenyl)benzo[d]oxazol-4-yl)-N,N-bis(pyridin-2-ylmethyl)methanamine (0.6 g, 0.77 mmol) in 10 mL of dry CH$_2$Cl$_2$ was cooled to −78° C. with dry ice/acetone. BBr$_3$ in CH$_2$Cl$_2$ (1M, 3 mL) was added dropwise under an argon atmosphere. The reaction mixture was stirred at −78° C. for 2 h and then at room temperature overnight. Following the addition of 4.0 ml distilled H$_2$O, the reaction mixture was stirred for additional 2 h and poured into a mixture of water (30 mL) and CH$_2$Cl$_2$ (30 mL). The organic layer was separated, and the aqueous layer was extracted twice with CH$_2$Cl$_2$ (60 ml). The combined organic layer was washed with brine and dried over anhydrous MgSO$_4$. After removal of the solvent on a rotary evaporator, the crude product was purified by recrystallization from MeOH/acetone (1:1), which give Zinhbo-5 as yellow power solid (0.08 g, 17.0%). $^1$H NMR (CD$_3$OD, 300 MHz, δ): 8.76 (d, J=5.7 Hz, 2H), 8.43 (t, J=7.8 Hz, 2H), 8.13 (d, J=8.4 Hz, 2H), 7.89 (t, J=6.3 Hz, 2H), 7.82 (s, 1H), 7.75 (d, J=8.7 Hz, 2H), 7.63 (m, 3H), 7.39 (m, 2H), 4.46 (s, 4H), 4.27 (s, 2H), 1.42 (s, 9H). $^1$H NMR (CDCl$_3$, 300 MHz, δ ppm): 11.16 (s, 1H), 10.34 (s, 1H), 8.86 (d, J=5.4 Hz, 2H), 8.42 (s, 2H), 8.30 (s, 2H), 7.84 (s, 2H), 7.80 (s, 1H), 7.78 (s, 1H), 7.58 (m, 3H), 7.53 (s, 1H), 7.50 (s, 1H), 7.24 (dd, J=8.4 Hz, J=7.8 Hz, 1H), 4.76 (s, 4H), 4.37 (s, 2H), 1.42 (s, 9H). $^{13}$C NMR (DMSO-d$_6$, δ ppm): 31.94, 35.31, 57.33, 115.49, 115.66, 116.00, 116.41, 124.60, 124.89, 125.43, 125.45, 126.64, 140.18, 147.67, 149.17, 149.60, 150.42, 150.44, 153.67, 161.46, 161.62. HRMS (ESI+) m/z: calcd for C$_{37}$H$_{34}$N$_5$O$_4$, 612.2611. found: 612.2582 (M)$^+$.

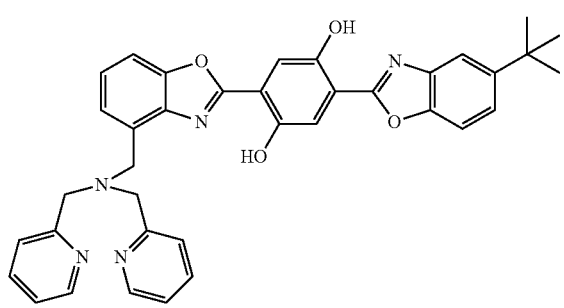

Zinhbo-5

A mixture of Zinhbo-5 and Zn(ClO$_4$)$_2$ (1:1 molar ratio) in ethanol was refluxed for 10 min. After slow evaporation of solvent at room temperature, the product gave needle-like crystals. Crystal structure revealed the ligand-to-metal ratio of 1:1 (FIG. 9). The structure shows that the zinc(II) cation is penta-coordinated in the complex.

What is claimed is:

1. A composition comprising a zinc ion coordinated to a Zinhbo derivative defined by the formula:

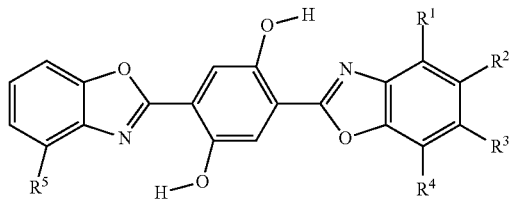

where R$^1$ is a hydrogen atom or an electron withdrawing group; R$^2$, R$^3$, and R$^4$ are each individually selected from the group consisting of a hydrogen atom, an electron withdrawing group, and an electron donating group; and R$^5$ is a chelator group capable of forming a complex with a zinc cation.

2. The composition of claim 1, where the electron donating group is an alkyl group.

3. The composition of claim 2, where the alkyl group is selected from the group consisting of methyl, ethyl, propyl, isopropyl, isobutyl, tertbutyl, n-butyl, sec-butyl, isopentyl, tertpentyl, n-pentyl, sec-pentyl, terthexyl, n-hexyl, isohexyl, and sec-hexyl.

4. The composition of claim 1, where the R$^5$ is a linear polyamine chelator or a cyclic polyamine chelator.

5. The composition of claim 1, where R$^1$, R$^3$, and R$^4$ are hydrogen atoms, and R$^2$ is an electron donating group.

6. The composition of claim 5, where the electron donating group is an alkyl group.

* * * * *